US008743369B2

(12) United States Patent
Ran et al.

(10) Patent No.: US 8,743,369 B2
(45) Date of Patent: *Jun. 3, 2014

(54) SURFACE PLASMON RESONANCE SENSOR

(71) Applicant: Bio-Rad Laboratories Inc., Hercules, CA (US)

(72) Inventors: Boaz Ran, Haifa (IL); Ariel G. Notcovich, Walnut Creek, CA (US); Ariel Lipson, Tel-Aviv (IL); Shay Nimri, Kibbutz Nir David (IL); Stephen G. Lipson, Haifa (IL); Doron Lipson, Chestnut Hill, MA (US)

(73) Assignee: Bio-Rad Laboratories Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/966,364

(22) Filed: Aug. 14, 2013

(65) Prior Publication Data
US 2013/0330838 A1 Dec. 12, 2013

Related U.S. Application Data

(60) Continuation of application No. 13/751,175, filed on Jan. 28, 2013, now abandoned, which is a continuation of application No. 13/348,663, filed on Jan. 12, 2012, now Pat. No. 8,363,223, which is a continuation of application No. 13/181,547, filed on Jul. 13, 2011, now Pat. No. 8,111,400, which is a division of application No. 12/535,707, filed on Aug. 5, 2009, now Pat. No. 7,999,942, which is a continuation of application No. 12/149,158, filed on Apr. 28, 2008, now Pat. No. 7,586,616, which is a division of application No. 10/540,940, filed as application No. PCT/IL02/01037 on Dec. 25, 2002, now Pat. No. 7,443,507.

(51) Int. Cl.
*G01N 21/55* (2014.01)

(52) U.S. Cl.
CPC .............. *G01N 21/553* (2013.01); *G01N 21/55* (2013.01)
USPC .......................................... 356/445

(58) Field of Classification Search
CPC ............................ G01N 21/553; G01N 21/55
USPC .......................................... 356/445–448, 344
See application file for complete search history.

(56) References Cited

U.S. PATENT DOCUMENTS

| 4,844,613 | A | 7/1989 | Batchelder et al. |
| 4,889,427 | A | 12/1989 | Van Veen et al. |
| 5,047,213 | A | 9/1991 | Finlan et al. |
| 5,313,264 | A | 5/1994 | Ivarsson et al. |

(Continued)

FOREIGN PATENT DOCUMENTS

| AU | 742417 | 1/2002 |
| EP | 0305109 | 3/1989 |

(Continued)

OTHER PUBLICATIONS

Communication Pursuant to Article 96(2) EPC Dated Nov. 2, 2007 From the European Patent Office Re.: Application No. 02808314.5.

(Continued)

*Primary Examiner* — Michael P Stafira

(57) ABSTRACT

An SPR sensor comprising a thin conducting layer comprising at least one conductive element formed on a surface of a transparent substrate, a light source that illuminates an interface between the conducting layer and the substrate, a photosensitive surface that generates signals from light reflected from the interface, a flow cell formed with at least one flow channel having a lumen defined by a wall formed from an elastic material and from a region of the conducting layer, and at least one hollow fluid-providing flow control apparatus having a lumen and an orifice communicating with its lumen. Fluid flow is enabled between the flow channel and the lumen of the flow control apparatus by forcing an end of the flow control apparatus through the elastic material so that the orifice communicates with the flow channel lumen.

14 Claims, 12 Drawing Sheets

(56) References Cited

U.S. PATENT DOCUMENTS

| | | | |
|---|---|---|---|
| 5,341,215 A | 8/1994 | Seher | |
| 5,633,724 A | 5/1997 | King et al. | |
| 5,694,930 A | 12/1997 | Pries et al. | |
| 5,770,462 A | 6/1998 | Molloy | |
| 5,812,272 A | 9/1998 | King et al. | |
| 5,907,408 A | 5/1999 | Naya et al. | |
| 5,917,607 A | 6/1999 | Naya | |
| 5,917,608 A | 6/1999 | Naya et al. | |
| 5,926,284 A | 7/1999 | Naya et al. | |
| 5,955,729 A | 9/1999 | Nelson et al. | |
| 6,008,893 A | 12/1999 | Roos et al. | |
| 6,268,125 B1 | 7/2001 | Perkins | |
| 6,326,612 B1 | 12/2001 | Elkind et al. | |
| 6,404,492 B1 | 6/2002 | Xu et al. | |
| 6,424,418 B2 | 7/2002 | Kawabata et al. | |
| 6,570,657 B1 | 5/2003 | Hoppe et al. | |
| 6,600,563 B1 | 7/2003 | Bahatt et al. | |
| 6,692,974 B2 | 2/2004 | Perkins | |
| 6,738,141 B1 | 5/2004 | Thirstrup | |
| 6,801,317 B2 | 10/2004 | Hofmann | |
| 6,873,417 B2 | 3/2005 | Bahatt et al. | |
| 7,251,085 B2 | 7/2007 | Bahatt et al. | |
| 7,443,507 B2 | 10/2008 | Ran et al. | |
| 7,535,570 B2 | 5/2009 | Muraishi | |
| 7,586,616 B2 | 9/2009 | Ran et al. | |
| 7,835,013 B2 | 11/2010 | Jones et al. | |
| 7,999,942 B2 | 8/2011 | Ran et al. | |
| 8,111,400 B2 | 2/2012 | Ran et al. | |
| 8,460,887 B2 * | 6/2013 | Goldberg et al. | 435/7.2 |
| 2002/0117517 A1 | 8/2002 | Unger et al. | |
| 2003/0076501 A1 | 4/2003 | Hofmann | |
| 2006/0072113 A1 | 4/2006 | Ran et al. | |
| 2008/0198384 A1 | 8/2008 | Ran et al. | |
| 2009/0296095 A1 | 12/2009 | Ran et al. | |
| 2012/0113428 A1 | 5/2012 | Ran et al. | |
| 2013/0196448 A1 | 8/2013 | Ran et al. | |

FOREIGN PATENT DOCUMENTS

| | | |
|---|---|---|
| EP | 0341928 | 11/1989 |
| EP | 0442921 | 8/1991 |
| EP | 0867697 | 9/1998 |
| EP | 0938661 | 9/1999 |
| EP | 1068511 | 1/2001 |
| JP | 01-224647 | 9/1989 |
| JP | 03-503806 | 8/1991 |
| JP | 09-126888 | 5/1997 |
| JP | 09-292332 | 11/1997 |
| JP | 09-292333 | 11/1997 |
| JP | 11-037929 | 2/1999 |
| JP | 11-044647 | 2/1999 |
| JP | 03-064313 | 7/2000 |
| JP | 2001-504582 | 4/2001 |
| JP | 2001-526386 | 12/2001 |
| JP | 03-294605 | 6/2002 |
| JP | 2002-540405 | 11/2002 |
| WO | WO 90/05317 | 5/1990 |
| WO | WO 90/09576 | 8/1990 |
| WO | WO 92/19984 | 11/1992 |
| WO | WO 98/22808 | 5/1998 |
| WO | WO 98/57149 | 12/1998 |
| WO | WO 99/30135 | 6/1999 |
| WO | WO 00/22419 | 4/2000 |
| WO | WO 01/20295 | 3/2001 |
| WO | WO 01/86262 | 11/2001 |
| WO | WO 02/36485 | 5/2002 |
| WO | WO 02/055993 | 7/2002 |
| WO | WO 02/063349 | 8/2002 |
| WO | WO 2004/059301 | 7/2004 |

OTHER PUBLICATIONS

Official Action Dated Jun. 15, 2007 From the US Patent and Trademark Office Re.: U.S. Appl. No. 10/540,940.
Official Action Dated Sep. 17, 2008 From the US Patent and Trademark Office Re.: U.S. Appl. No. 12/149,158.
Translation of Notice of Reason(s) for Rejection Dated Nov. 30, 2007 From the Japanese Patent Office Re.: Application No. 2004-563535.
Communication Pursuant to Article 96(2) EPC Dated Nov. 30, 2006 From the European Patent Office Re.: Application No. 02808314.5.
Communication Relating to the Result of the Partial International Search Report Dated Oct. 23, 2003 From the International Searching Authority Re.: Application No. PCT/IL02/01037.
International Preliminary Examination Report Dated Mar. 24, 2005 From the European Patent Office Re.: Application No. PCT/IL02/01037.
International Search Report Dated Jan. 14, 2004 From the International Searching Authority Re.: Application No. 02808314.5.
Notice of Allowance Dated May 1, 2009 From the US Patent and Trademark Office Re.: U.S. Appl. No. 12/149,158.
Notice of Allowance Dated Jun. 4, 2008 From the US Patent and Trademark Office Re.: U.S. Appl. No. 10/540,940.
Notice of Allowance Dated Oct. 7, 2011 From the US Patent and Trademark Office Re. U.S. Appl. No. 13/181,547.
Notice of Allowance Dated May 14, 2013 From the US Patent and Trademark Office Re. U.S. Appl. No. 13/751,175.
Notice of Allowance Dated Apr. 18, 2011 From the US Patent and Trademark Office Re.: U.S. Appl. No. 12/535,707.
Notice of Allowance Dated Sep. 28, 2012 From the US Patent and Trademark Office Re. U.S. Appl. No. 13/348,663.
Notice of Allowance Dated Jan. 29, 2008 From the US Patent and Trademark Office Re.: U.S. Appl. No. 10/540,940.
Notification of Reasons of Rejection Dated Jan. 29, 2009 From the Japanese Patent Office Re.: Application No. 2004-563535 and Its Translation Into English.
Official Action Dated Aug. 13, 2010 From the US Patent and Trademark Office Re.: U.S. Appl. No. 12/535,707.
Official Action Dated Nov. 24, 2010 From the US Patent and Trademark Office Re.: U.S. Appl. No. 12/535,707.
Official Action Dated Feb. 29, 2012 From the US Patent and Trademark Office Re. U.S. Appl. No. 13/348,663.
Official Action Dated Nov. 30, 2007 From the Japanese Patent Office Re.: Application No. 2004-563535 and Its Translation Into English.
Requisition by the Examiner Dated Oct. 5, 2009 From the Canadian Intellectual Property Office Re.: Application No. 2,511,934.
Response Dated Sep. 7, 2010 to Official Action of Aug. 13, 2010 From the US Patent and Trademark Office Re.: U.S. Appl. No. 12/535,707.
Response Dated Feb. 24, 2011 to Official Action of Nov. 24, 2010 From the US Patent and Trademark Office Re.: U.S. Appl. No. 12/535,707.
Written Opinion Dated Nov. 23, 2004 From the International Searching Authority Re.: Application No. PCT/IL02/01037.
Anonymous "BIAcore Surface Plasmon Resonance (SPR)", 3 P., 2002. http://www.astbury.leeds.ac.uk/Facil/spr.htm.
Berger et al. "Surface Plasmon Propagation Near an Index Step", MESA Institute, Applied Optics Group, University of Twente, p. 1-10, 2002, http://lps.ens.fr/~berger/articles/art4/OptComm/htm.
Berger et al. "Surface Plasmon Resonance Multisensing", Analytical Chemistry, 70(4): 703-706, 1998.
Grigorenko et al. "Dark-Field Surface Plasmon Resonance Microscopy", Optics Communications, 174: 151-155, 2000.
Grigorenko et al. "Phase Jumps and Interferometric Surface Plasmon Resonance Imaging", Applied Physics Letters, 75(25): 3917-3919, 1999.
Herminghaus et al. "Phase Contrast Surface Mode Resonance Microscopy", Quantum Electronics, 112: 16-20, 1994.
Homola et al. "Surface Plasmon Resonance Sensors: Review", Sensors and Actuators, B 54: 3-15, 1999.
Jordan et al. "Surface Plasmon Resonance Imaging Measurements of Electrostatic Biopolymer Adsorption Onto Chemically Modified Gold Surfaces", Analytical Chemistry, 69(7): 1449-1456, 1997.
Kabashin et al. "Interferometer Based on a Surface-Plasmon Resonance for Sensor Applications", Quantum Electronics, 27(7): 653-654, 1997.

(56) References Cited

OTHER PUBLICATIONS

Kabashin et al. "Phase—Polarisation Contrast for Surface Plasmon Resonance Biosensors", Biosensors & Bioelectronics, 13: 1263-1269, 1998.

Kabashin et al. "Surface Plasmon Resonance Bio-and Chemical-Sensors With Phase-Polarisation Contrast", Sensors and Actuators, B 54: 51-56, 1999.

Kabashin et al. "Surface Plasmon Resonance Interferometer for Bio- and Chemical-Sensors", Optics Comminications, 150: 5-8, 1998.

Kochergin et al. "Phase Properties of a Surface-Plasmon Resonance From the Viewpoint of Sensor Applications", Quantum Electronics, vol. 28(5): 444-448, 1998.

Kochergin et al. "Visualisation of the Angular Dependence of the Reflected-Radiation Phase Under Conditions of a Surface-Plasmon Resonance and its Sensor Applications", Quantum Electronics, 28(9): 835-839, 1998.

Lipson "Experiment Procedure", ProteOptics, Haifa, IL, 2 P. 2002.

Lofas et al. "Bioanalysis With Surface Plasmon Resonance", Sensors and Actuators B Chemical, 5(1/4): 79-84, 1991. p. 79, col. 2, Par.2-p. 81, col. 1, Par.2.

Marszalec "Modelling and Simulation of an Angular-Scan LED Array-Based Range Imaging Sensor", Proceedings of the 1993 IEEE/RSJ International Conference on Intelligent Robots and Systems, Yokohama, JP, p. 1837-1844, 1993.

Marszalec et al. "A LED-Array-Based Range-Imaging Sensor for Fast Three-Dimensional Shape Measurments", Sensors and Actuators A, 46-47: 501-505, 1995.

Marszalec et al. "A Photoelectric Range Scanner Using an Array of LED Chips", Proceedings of the 1992 IEEE International Conference on Robots and Automation, Nice, FR, p. 593-598, 1992.

Nikitin et al. "Surface Plasmon Resonance Interferometry for Biological and Chemical Sensing", Sensors and Actuators, B 54: 43-50, 1999.

Nikitin et al. "Surface Plasmon Resonance Interferometry for Micro-Array Biosensing", Eurosensors XIII, The 13th European Conference on Solid-State Transducers, The Hague, NL, Optical Techniques in (Bio)Chemical Systems, 5A4: 235-238, 1999.

Notcovich et al. "Surface Plasmon Resonance Phase Imaging", Applied Physics Letters, 76(13): 1665-1667, 2000.

Teng et al. "Simple Reflection Technique for Measuring the Electro-Optic Coefficient of Poled Polymers", Applied Physics Letters, 56 (18): 1734-1736, 1990.

Texas Instruments "Refractive Index Sensing With Surface Plasmon Resonance: The Kretschmann Geometry", Spreeta Technology Overview, 2 P., 2001.

Totzeck et al. "Phase—Shifting Polarization Interferometry for Microstructure Linewidth Measurement", Optic Letters, 24(5): 294-296, 1999.

Wegner et al. "An Introduction to SPR-Surface Plasmon Resonance", 2 P., 2002. http://www.uksaf.org/tech/spr.html.

\* cited by examiner

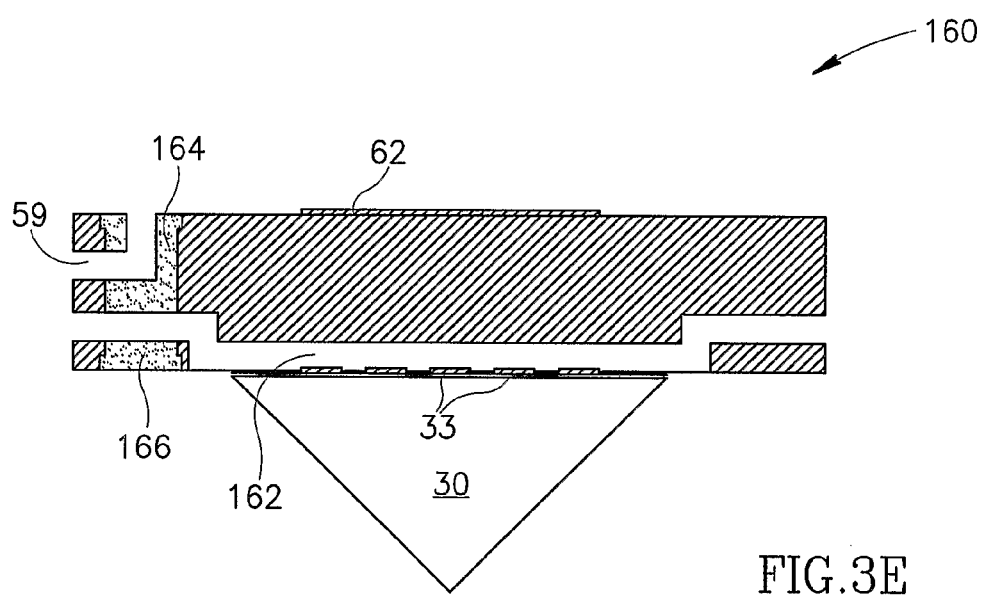

SURFACE PLASMON RESONANCE SENSOR

RELATED APPLICATIONS

This application is a continuation of U.S. patent application Ser. No. 13/751,175 filed on Jan. 28, 2013, which is a continuation of U.S. patent application Ser. No. 13/348,663 filed on Jan. 12, 2012, now U.S. Pat. No. 8,363,223, which is a continuation of U.S. patent application Ser. No. 13/181,547 filed on Jul. 13, 2011, now U.S. Pat. No. 8,111,400, which is a division of U.S. patent application Ser. No. 12/535,707 filed on Aug. 5, 2009, now U.S. Pat. No. 7,999,942, which is a continuation of U.S. patent application Ser. No. 12/149,158 filed on Apr. 28, 2008, now U.S. Pat. No. 7,586,616, which is a division of U.S. patent application Ser. No. 10/540,940 filed on Jun. 23, 2005, now U.S. Pat. No. 7,443,507, which is a National Phase of PCT Patent Application No. PCT/IL2002/001037 filed on Dec. 25, 2002. The contents of all of the above applications are incorporated herein by reference.

FIELD OF THE INVENTION

The invention relates to surface plasmon resonance (SPR) sensors and in particular to methods and apparatus for forming a probe layer on an SPR sensor surface, illuminating an SPR sensor surface and controlling liquid flow in an SPR sensor.

BACKGROUND OF THE INVENTION

SPR sensors generate optical signals responsive to the dielectric constant and/or thickness, hereinafter referred to collectively as "optical properties", of regions of a layer, hereinafter referred to as a "probe layer", of material contiguous with a thin layer of conducting material. The thin conductive layer, hereinafter an "SPR conductor", typically has a thickness less than about 100 nm and is generally formed from a metal, usually silver or gold, on a surface of a transparent substrate such as glass. The surface on which the SPR conductor is formed is hereinafter referred to as a "sensor surface".

Optionally, such as in a Kretschmann configuration of an SPR sensor, the sensor surface is a first surface of a prism having a triangular cross section. Light from a suitable light source is directed into the prism through a second surface of the prism so that the light is incident at a non-zero angle of incidence on the SPR conductor from inside the prism. The light is linearly polarized so that it has a "p" component of polarization. The SPR conductor is sufficiently thin so that for angles greater than the critical angle of the light at the interface between the prism and the SPR conductor, the evanescent field of the light extends substantially into the probe layer. Light from the incident light is reflected from interface between the sensor surface and the SPR conductor, exits the prism through a third surface of the prism and is detected by a suitable photosurface, such as for example a CCD.

For a given wavelength of the incident light, there exists a particular angle, hereinafter a "resonance angle", greater than the critical angle, for which the evanescent field of the p polarization component of the light resonates with a propagation mode of charge density waves of electrons in the SPR conductor. The charge density waves tend to propagate along the surfaces of the SPR conductor and are conventionally referred to as "surface plasmons". At the resonance angle and angles within an "angular resonance width", in a neighborhood of the resonance angle, energy is coupled from the evanescent field into surface plasmons.

As a result of energy absorbed from the evanescent field by the surface plasmons, for the given wavelength, reflectance of the light as a function of incident angle decreases substantially for angles within the angular width of the plasmon resonance and exhibits a local minimum at the resonance angle. In addition, phase of reflected light as a function of angle undergoes relatively rapid change for angles within the angular width of the plasmon resonance.

Similarly, for a given incident angle of the incident light, there exists a particular resonance wavelength at which the incident light resonates with a surface plasmon in the SPR conductive layer. Reflectance of the light as a function of wavelength decreases substantially for wavelengths within a "wavelength resonance width" of the surface plasmon and exhibits a local minimum at the resonance wavelength for the given angle of incidence. Phase of reflected light as a function of wavelength undergoes relatively rapid change for wavelengths within the wavelength resonance width.

The SPR resonance angle, resonance wavelength, reflectance and phase changes that characterize a surface plasmon resonance are hereinafter referred to as "SPR parameters". The SPR parameters are functions of the optical properties of the substrate (e.g. the prism glass), the SPR conductor and, because the evanescent field extends into the probe layer, of the probe layer.

In typical operation of an SPR sensor, generally either the wavelength of light incident on the sensor surface is maintained constant and the incident angle of the light varied or the incident angle is maintained constant and the wavelength varied. Signals generated by the photosurface responsive to the light reflected to the photosurface from a region of the sensor surface under either of these conditions are used to determine a value of at least one SPR parameter for the region. The at least one SPR parameter is used to determine a characteristic of a material, hereinafter a "target material", that affects the index of refraction of the probe layer by interacting with the probe layer. The target material is generally a liquid or a gas, i.e. a target liquid or target gas, that is transported along a surface of the probe layer by a suitable "flow cell".

For example, in some applications an SPR parameter is used to identify and assay analytes in a target liquid or gas that flows over the sensor surface of an SPR sensor and interact with components of the probe layer to change at least one the probe layer's optical properties. In some applications an SPR parameter is used to determine a characteristic of an interaction, such as for example an interaction rate, between material in a probe layer and a target material that affects the an optical property of the probe layer. The rate of interaction determines a rate at which the optical property of the probe layer changes and thereby a rate of change of an SPR parameter determined by the SPR sensor. The determined rate of change of the SPR parameter is used to determine the rate of interaction.

SPR sensors and methods are generally very sensitive to changes in an optical property of a probe layer and have proven to be useful in detecting changes in an optical property of a probe layer generated by relatively small stimuli. An SPR probe layer may also be configured as a multianalyte "microarray" that presents on each of a relatively large plurality of different relatively small regions, "microspots", of a sensor surface a different probe material for interaction with a target material. Thus, for example an SPR probe layer can be configured for assaying a relatively large plurality of different analytes or for characterizing a relatively large plurality of interactions. As a result, SPR sensors and methods are finding increasing use in biochemical applications and SPR sensors and methods are used to identify and assay biomolecules and characterize reactions between biomolecules.

An article by Charles E. H. Berger et al. entitled "Surface Plasmon Resonance Multisensing", Anal. Chem. Vol. 70, February 1998, pp 703-706, the disclosure of which is incorporated herein by reference, describes an SPR sensor and method that are used to characterize binding of antigens to antibodies. The SPR sensor has a gold SPR conductor formed on a surface, i.e. a sensor surface, of a glass plate, which is optically coupled to a prism. A flow cell comprising four parallel linear "microchannels" (generally, flow channels having at least one dimension about equal to or smaller than a millimeter), each 1 mm wide, 10 mm long and about 0.1 mm deep, is positioned over the SPR conductor. A different antibody is pumped through each microchannel and adsorbed on the gold conductor to form a probe layer. The resulting multi-analyte probe layer comprises a linear array of four different antibodies, each immobilized in a different "antibody" strip on the SPR conductor.

The flow cell is then repositioned so that the microchannels are perpendicular to the antibody strips. A different antigen is pumped through each of the microchannels. Each of the antigens thus comes into contact with each of the four antibodies adsorbed onto the gold conductor. To an extent that the antigen binds with a particular one of the antibodies, it changes an optical property of a region of the antibody strip on which the particular antibody that contacts the antigen is located. Rates at which each antigen of the four antigens binds to each of the four antibodies are determined from measurements of changes in reflectance for light incident on the sensor surface at an angle near to an SPR resonance angle. The article notes that whereas the probe layer was formed by flowing antibodies through microchannels, other methods for forming the probe layer, such as by depositing small quantities of antigen in specific locations using an ink jet nozzle, may be used.

PCT publication WO 02/055993, the disclosure of which is incorporated herein by reference, notes that "electrostatic fields can be used for controlling the extent of immobilization or attachment of biomolecules, such as thiol-derivitized oligonucleotides", to a surface. The book "Microarray Analysis", by Mark Schena, John Wiley and Sons, Inc. 2003, the disclosure of which is incorporated herein by reference, describes various methods for depositing or creating small quantities of desired ligands in microspots on a surface to manufacture microarrays. Among the methods described, for example in chapter seven of the book, are contact and non-contact printing methods and photolithographic methods.

U.S. Pat. No. 5,313,264, the disclosure of which is incorporated herein by reference, describes an SPR sensor having a "liquid handling block" comprising a network of microconduits and valves. The network of microconduits and valves is used for moving suitable liquids containing probe material across an SPR conductor formed on a sensor surface so as to generate a probe layer on the SPR conductor and subsequently for moving a target liquid over the probe layer.

The SPR sensor also comprises a substantially monochromatic light source and an optical system for generating a wedge-shaped converging beam from light provided by the light source and directing the wedge-beam onto the sensor surface. The wedge-beam illuminates the probe layer along a spatially fixed, relatively narrow strip-shaped region of the sensor surface with light that is simultaneously incident on the region in a range of incident angles. The range of incident angles is determined by an angle of convergence of the wedge-beam. Light reflected from the sensor surface is imaged on a "two dimensional photodetector device". Signals provided by the photodetector device are processed to provide a measurement of a change in the refractive index of the probe layer due to interaction of material in the probe layer with material in a target solution that is transported along the probe layer by the liquid handling block.

Many conventional SPR methods and apparatus for forming probe layers, flowing liquids over probe layer surfaces and optically scanning sensor surfaces are relatively complicated, expensive and/or time consuming. Alternative SPR sensors and methods for generating multi-analyte probe layers, pumping liquids over probe layers and illuminating sensor surfaces are needed.

SUMMARY OF THE INVENTION

An aspect of some embodiments of the present invention relates to providing a new SPR sensor for simultaneously determining a characteristic of each of a plurality of different interactions between probe and target materials and/or identifying a plurality of different components in target materials.

An aspect of some embodiments of the present invention relates to providing methods and apparatus for producing a microarray probe layer in an SPR sensor.

In accordance with some embodiments of the present invention, an SPR conductor in the SPR sensor comprises a plurality of conducting elements formed on a sensor surface of a suitable substrate. Optionally, the conducting elements comprise a plurality of parallel conducting strips. A flow apparatus in the SPR sensor comprises a flow cell having a plurality of optionally parallel flow microchannels formed on a surface of the flow cell. The flow cell is positioned on the sensor surface so that each microchannel crosses over each of the conducting strips and liquid flowing in each of the flow channels contacts each of the strips. Optionally, the flow channels are perpendicular to the strip conductors. A region of a strip conductor over which a flow channel crosses is referred to as a "crossover region".

Each of the conducting strips, hereinafter "strip electrodes", is connected to a power supply so that each strip electrode may be electrified relative to a suitable reference electrode independent of electrification of the other of the plurality of electrodes. When a strip electrode is electrified it generates an electric field in the microchannels. Depending upon the direction of the electric field and charge or charge distribution carried by ligands in liquids flowing through the microchannels, the ligands may be attracted to or repelled from the electrode.

To immobilize a desired ligand on a particular crossover region of a given electrode, a liquid containing the desired ligand is pumped through the microchannel that crosses over the particular crossover region. The given strip electrode is electrified to attract the desired ligand to the electrode so that the ligand settles on and bonds to the electrode at the crossover region. If it is desired to prevent the ligand from accumulating at crossover regions of the other strip electrodes that the flow channel crosses over, the other electrodes are electrified so as to repel the ligand. By flowing appropriate ligands through appropriate flow channels and electrifying strip electrodes appropriately, a microarray of substantially any pattern of immobilized ligands can be produced.

In accordance with an embodiment of the present invention subsequent to creating the microarray, a suitable buffer solution is flushed through the microchannel to wash away non-immobilized ligands and target solutions that are to be examined by the SPR sensor are pumped through the microchannels. Unlike in prior art such as described in the article by Charles E. H. Berger et al. entitled "Surface Plasmon Resonance Multisensing" noted above, to examine target solutions with the microarray the flow cell does not have to be reoriented relative to the microarray after its production.

In some embodiments of the present invention, the conducting elements comprised in the SPR conductor are relatively small conducting "pixel electrodes". Each flow channel crosses over at least one pixel electrode and each pixel electrode is located under a single flow channel. Each pixel electrode is connected to a power supply using methods known in the art so that the power supply can electrify the pixel independently of electrification of the other pixel electrodes. Ligands having a suitable charge or a charge distribution comprised in liquids flowing through the microchannels may be attracted to or repelled from a given pixel electrode by appropriately electrifying the pixel electrode.

An aspect of some embodiments of the present invention relates to providing "flow apparatus" for controlling flow of liquids in an SPR sensor that provides and/or prevents liquid flow into a microchannel at a localized region of the microchannel without use of a valve at the region. The localized region is referred to as a "flow control region".

In accordance with an embodiment of the present invention, the microchannel is defined by a wall, which at the flow control region, is formed from an elastic material. In some embodiments of the present invention the microchannel is formed in a flow cell formed from an elastic material. In some embodiments of the present invention, the microchannel is formed in a flow cell produced from a non-elastic material having an insert formed from an elastic material. The elastic insert forms at least a portion of the wall of the microchannel located at the flow control region.

In accordance with an embodiment of the present invention a hollow needle, such as for example a syringe needle, hereinafter referred to as a "flow needle", having an orifice that communicates with the needle's lumen is used to control gas or liquid flow at the junction region. The elastic material at the flow control region is punctured by the needle and the needle pushed into the channel so that it at least partially protrudes into the channel's lumen with the needle orifice substantially aligned with the channel lumen. A gas or liquid fluid is pumped into or aspirated from the microchannel through the needle via the needle orifice by any of many suitable devices and methods known in the art, such as a pump or pumps.

In some embodiments of the present invention the needle, when introduced into the microchannel lumen functions as a baffle that at least partially blocks fluid flow into a downstream portion of the microchannel from an upstream portion of the microchannel or from another microchannel.

In accordance with an embodiment of the present invention, upon sufficient extraction of the needle from the microchannel and the elastic substrate material, the elastic material substantially seals a hole formed therein as a result of insertion of the needle into the microchannel. As a result, a configuration of microchannel connections disturbed by the insertion of the needle is returned upon extraction of the needle substantially to the way it was prior to the disturbance.

In some embodiments of the present invention the needle is formed with a depression, hereinafter referred to as a "shunt depression", in the needle's wall. Upon sufficient penetration of the needle into the microchannel lumen, the shunt depression is substantially aligned with the microchannel and functions as a "shunt" microchannel that connects an upstream portion of the microchannel with another microchannel. The shunt depression shunts flow of liquid from the upstream portion to the other channel.

It is noted that a "valveless" flow cell produced in accordance with an embodiment of the present invention is expected to be generally less expensive to produce than prior art flow cells comprising valves to control liquid flow. As a result, a flow cell made in accordance with an embodiment of the present invention may be sufficiently inexpensive to be disposable after being used once. By using a "disposable" flow cell once, possibility of contamination of fluids that are pumped through the flow cell may be reduced.

An aspect of some embodiments of the present invention relates to providing an illumination system for SPR sensors for illuminating a same relatively large region of a sensor surface with light at a same wavelength at each of a plurality of selectable angles of incidence. In accordance with an embodiment of the present invention, the illumination system does not require moving components to select different ones of the plurality of incident angles.

An aspect of some embodiments of the present invention relates to providing an illumination system for SPR sensors for illuminating a same relatively large region of an SPR sensor surface at a same angle of incidence with light at each of a plurality of selectable wavelengths. In accordance with an embodiment of the present invention, the illumination system does not require moving components to select different ones of the plurality of wavelengths.

In accordance with an embodiment of the present invention, an illumination system comprises an array of light sources. An optical system collimates light from any given light source in the array into a beam of substantially parallel light rays all of which are incident on the sensor surface at substantially a same incident angle. The incident angle is a function of the position of the light source.

In some embodiments of the present invention, for at least a subset of the light sources in the array, the positions of the light sources are such that the incident angle for different light sources is different. Each of the light sources in the at least a subset provides light at a same wavelength. The sensor surface is illuminated with light at the wavelength and different incident angles by suitably turning on and turning off light sources in the at least a subset of light sources.

In some embodiments of the present invention for at least a subset of the light sources the positions of the light sources are such that the incident angle for each of the light sources is substantially the same. Each of the light sources in the at least a subset provides light at a different wavelength. The sensor surface is illuminated with light at the incident angle and different wavelengths by suitably turning on and turning off light sources in the at least a subset of light sources.

There is therefore provided in accordance with an embodiment of the present invention, an SPR sensor comprising: a thin conducting layer comprising at least one conductive element formed on a surface of a transparent substrate; an illumination system controllable to illuminate an interface between the conducting layer and the substrate; a photosensitive surface that generates signals responsive to light from the light source that is reflected from a region of the interface; a flow cell formed with at least one flow channel having a lumen defined by a wall at least a portion of which is formed from an elastic material and a portion of which is formed by a region of the conducting layer; and at least one hollow needle having an exit orifice communicating with the needle's lumen and wherein fluid flow is enabled between the flow channel and the needle's lumen by puncturing the elastic material with the at least one needle so that the exit orifice communicates with the flow channel lumen.

Optionally, the flows cell is produced from of an elastic material.

In some embodiments of the present invention, the flow cell is formed from a relatively non-elastic material having an insert formed from an elastic material and wherein material of the insert forms at least a portion of the wall of the at least one flow channel.

In some embodiments of the present invention the end of the needle is closed and the exit orifice is located along the length of the needle.

In some embodiments of the present invention when the needle protrudes into the channel it at least partially blocks flow of a fluid from a portion of the channel upstream of the needle to a portion of the needle downstream of the needle. Optionally, when the needle protrudes into the channel, the needle blocks substantially all fluid flow from the upstream portion to the downstream portion of the channel.

In some embodiments of the present invention, the needle is formed with a depression in the needle wall and wherein when the needle protrudes into the channel the depression forms a shunt channel between the upstream portion of the channel and another channel and at least a portion of a liquid flowing from the upstream portion of the channel towards the downstream portion is shunted through the shunt channel to the other channel.

In some embodiments of the present invention, upon extraction of the needle a sufficient distance from the elastic material a hole made in the elastic material as a result of the puncturing seals.

In some embodiments of the present invention, the at least one needle comprises at least two needles for a channel of the at least one channel and to cause a fluid to flow in the channel both needles puncture the elastic material and are positioned to protrude into the channel with their respective orifices communicating with the channel lumen so that fluid may be pumped into the channel via one of the needles and aspirated from the channel via the other of the needles. Optionally, the channel is a blind channel having neither an inlet or outlet orifice.

In some embodiments of the present invention the SPR sensor comprises a fluid pump coupled to the at least one needle controllable to pump fluid into the needle and thereby, when the needle orifice communicates with the flow channel lumen, into the flow channel.

In some embodiments of the present invention, the SPR sensor comprises a fluid pump coupled to the at least one needle controllable to aspirate fluid from the needle and thereby, when the needle orifice communicates with the flow channel, from the flow channel.

In some embodiments of the present invention, the illumination system comprises: an array of light sources; a collimator that directs light from each light source in a collimated beam of light that enters the substrate and is incident on a region of the interface between the substrate and conducting layer region that forms the wall portion of each of the at least one flow channel; and a light source controller controllable to turn off and turn on a light source in the array independent of the other light sources in the array.

There is further provided in accordance with an embodiment of the present invention, an SPR sensor comprising: a thin conducting layer comprising at least one conductive element formed on a surface of a transparent substrate; a flow cell formed with at least one flow channel having a lumen defined by a wall a portion of which is formed by a region the conducting layer; a photosensitive surface that generates signals responsive to light reflected from a region of the interface between the region of the conducting layer that forms the wall portion of each of the at least one flow channel and the substrate; and an illumination system comprising: an array of light sources; a collimator that directs light from each light source in a collimated beam of light that enters the substrate and is incident on a region of the interface between the substrate and conducting layer region that forms the wall portion of each of the at least one flow channel; and a light source controller controllable to turn off and turn on a light source in the array independent of the other light sources in the array.

Additionally or alternatively, the array is a linear array having an array axis. Optionally, the axis of the array and a normal to the interface are substantially coplanar. Alternatively, the axis of the array and the normal are optionally substantially perpendicular.

In some embodiments of the present invention the array is a two dimensional array. Optionally, the array comprises rows and columns of light sources. Optionally, each column is substantially coplanar with a normal to the interface. Alternatively or additionally, each row is substantially perpendicular to the normal.

In some embodiments of the present invention light sources in a same column provide light at substantially same wavelengths.

In some embodiments of the present invention all the light sources in the array provide light at substantially same wavelengths.

In some embodiments of the present invention, light sources in a same row provide light at different wavelengths.

In some embodiments of the present invention the SPR sensor comprises an optical element having two parallel surfaces through which light from each light sources passes before it is incident on the interface and wherein the optical element is rotatable about an axis perpendicular to the normal so as to change an angle at which light from a given light source is incident on the interface.

In some embodiments of the present invention the at least one conductive element comprises a plurality of conductive elements.

There is further provided, in accordance with an embodiment of the present invention, an SPR sensor comprising: a thin conducting layer comprising a plurality of conducting elements formed on a surface of a transparent substrate; an illumination system controllable to illuminate an interface between the conducting layer and the substrate; a photosensitive surface that generates signals responsive to light from the light source that is reflected from a region of the interface; and a flow cell formed with at least one flow channel having a lumen defined by a wall a portion of which is formed by a region the conducting layer.

Additionally or alternatively, each conductive element is connected to a power source controllable to electrify the conducting element with respect to a reference electrode.

In some embodiments of the present invention, the plurality of conductive element comprises a plurality of conducting strips. Optionally, each of the at least one flow channel crosses over each conducting strip.

In some embodiments of the present invention, the plurality of conductive elements comprises a plurality of conducting pixels. Optionally, each of the at least one flow channel passes over at least one conducing pixel and each pixel lies under a flow channel.

In some embodiments of the present invention the SPR sensor comprises an exclusive reference electrode for each conducting element relative to which the conducting element is electrified.

In some embodiments of the present invention all the conducting elements are electrified relative to a same reference electrode.

Alternatively or additionally, the reference electrode is located on an external surface of the flow cell.

In some embodiments of the present invention the reference electrode is located inside the material from which the flow cell is formed.

In some embodiments of the present invention the reference electrode is located on the surface of the substrate. Optionally, the reference electrode is comb shaped having parallel conducting teeth connected to a common backbone. Optionally, the conductive elements are located between the conducting teeth.

In some embodiments of the present invention, the flow channel has a cross section area less than or equal to about a square millimeter. Optionally, the flow channel has a cross section area less than or equal to about 0.5 square millimeters. Optionally, the flow channel has a cross section area less than or equal to about 0.2 square millimeters. Optionally, the flow channel has a cross section area less than or equal to about 0.1 square millimeters.

In some embodiments of the present invention the at least one flow channel comprises a plurality of channels.

BRIEF DESCRIPTION OF FIGURES

Non-limiting examples of embodiments of the present invention are described below with reference to figures attached hereto and listed below. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

FIG. 3E schematically shows a cross sectional view of a flow cell having a microchannel and elastic inserts, in accordance with an embodiment of the present invention;

DETAILED DESCRIPTION OF EXEMPLARY EMBODIMENTS

Figure 1A:
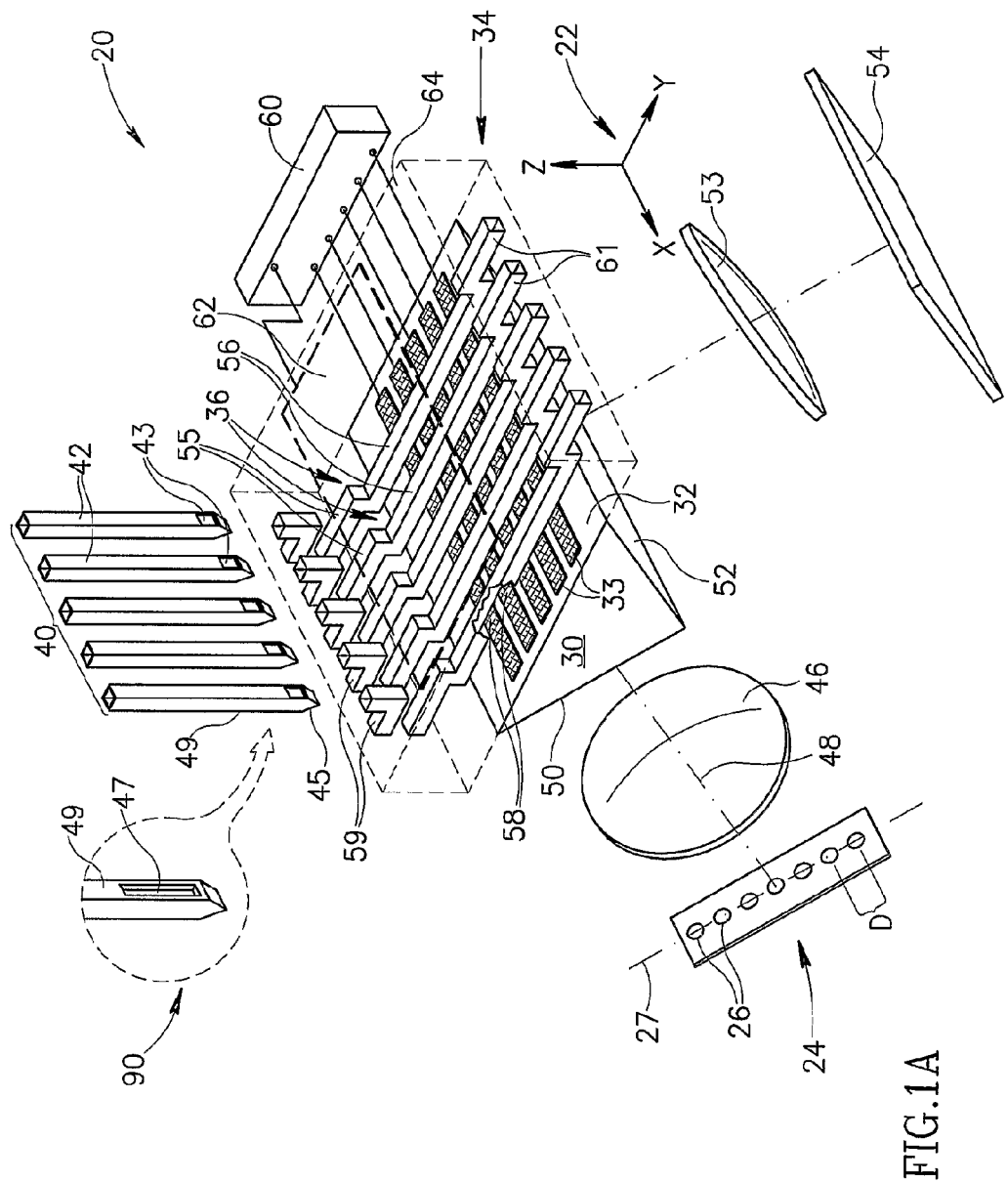
FIGS. 1A-1F schematically show SPR sensor, in accordance with embodiments of the present invention.

FIG. 1A schematically shows an SPR sensor 20 in accordance with an embodiment of the present invention. For convenience of discussion location and position of elements and features of SPR sensor 20 are referred to a coordinate system 22.

SPR sensor 20 comprises an optionally linear array 24 of light sources 26 having an array axis 27 and a prism 30 having a sensor surface 32. A flow cell 34 comprises microchannels 36 for flowing liquid across and in contact with sensor surface 32 and a probe layer (not shown) of desired ligands generated on a suitable SPR conductor formed on the sensor surface. In SPR sensor 20 the probe layer is generated on an SPR conductor optionally comprising a plurality of strip electrodes 33.

An array 40 of flow needles 42 coupled to suitable pumping apparatus (not shown) is optionally used to introduce liquids into microchannels 36. Operation of flow needles 42 in introducing liquid into microchannels 36 is described below. Microchannels 36 and flow needles 42 are shown having square or rectangular cross sections for convenience of presentation and cross section shapes of the microchannels and flow needles, in accordance with an embodiment of the present invention may have cross section shapes other than square or rectangular. For example, the cross section shapes may be round, oval or irregular. In addition, the sharp rectangular bends in microchannels 36 may be rounded and gradual. In some configurations of microchannels in accordance with embodiments of the present invention, bends such as though shown in FIG. 1A, may not exist.

Microchannels 36 optionally have a cross section less than or equal to about 1 sq.-mm. Optionally the microchannel has a cross section less than or equal to about 0.5 sq.-mm. Optionally the microchannel cross section is less than about 0.2 sq.-mm. Optionally the microchannel cross section is less than about 0.1 sq.-mm.

The outer form of flow cell 34 is shown in ghost lines and details of internal features, such as microchannels 36, of the flow cell are shown in solid lines for clarity of presentation. Sensor surface 32 is arbitrarily located in the xy-plane of coordinate system 22, light sources 26 provide light at a same wavelength appropriate for intended SPR angular scan applications and array axis 27 of linear array 24 optionally lies in the yz-plane.

Linear array 24 is positioned at the focal plane of an optical system schematically represented by a lens 46 having an optical axis 48 in the yz-plane. Lens 46 collects and collimates light from each light source 26 into a beam of parallel light rays and directs the collimated light so that it is incident on an "input" prism surface 50 of prism 30. A normal to input surface 50 is optionally parallel to the yz-plane. Light directed by collimator 46 that is incident on input surface 50 enters prism 30 and is incident on sensor surface 32.

All light incident on sensor surface 32 from a given light source 26 is incident on the sensor surface at substantially a same incident angle and light from different light sources 26 is incident on the sensor surface at different incident angles. The angle at which light from a given light source 26 is incident on sensor surface 32 is determined by the position of the given light source along the axis of linear array 24, the focal length "f" of lens 46 and the index of refraction "n" of material from which prism 30 is formed. An angular difference between the angles of incidence on sensor surface 32 of light from two adjacent light sources 26 is approximately equal to $(D/f)(1/n)$, where D is a distance between the adjacent light sources 26. Optionally, distance D between any two adjacent light sources 26 along array axis 27 is the same.

It is noted that incident angles available from light source array 24 are "quantized" in steps of $(D/f)(1/n)$ radians. In some embodiments of the present invention, an SPR sensor such as SPR sensor 21 shown in FIG. 1B, comprises a "displacement plate" 100 formed from a suitably transparent material and having parallel surfaces 101 and 102 is positioned between light source array 24 and prism 30. Except for displacement plate 100, SPR sensor 21 is identical to SPR sensor 20. Displacement plate 100 is optionally positioned between light source array 24 and lens 46 and is controllable to be rotated about an axis 104 parallel to the x-axis. Angular orientation of displacement plate 100 is thereby controllable so that a normal (not shown) to surfaces 101 and 102 can be oriented at a desired angle with respect to optic axis 48.

For non-zero "displacement angles" between optic axis 48 and the normal to surfaces 101 and 102, displacement plate 100 generates virtual images of light sources 26 that are displaced along array axis 27. Magnitude of displacement of light sources 26 is a function of the displacement angle, distance between surfaces 101 and 102 and index of refraction of the material from which displacement plate 100 is formed. By suitably rotating displacement plate 100, light from any light source 26 can be directed to be incident on sensor surface 32 at substantially any desired incident angle and not only at a quantized incident angle.

Light incident on sensor surface 32 that is reflected from the surface exits prism 30 through an output prism surface 52 and is collected and imaged by a suitable optical system represented by a lens 53 onto a two dimensional photosurface 54 such as a CCD. A polarizer (not shown) is positioned between array 24 and prism 30 or preferably between prism 30 and photosurface 54. The polarizer linearly polarizes light received by photosurface 54 so that relative to sensor surface 32 it has substantially only a p component of polarization.

Whereas the SPR conductor shown in FIG. 1A (and FIG. 1B, however FIG. 1A will generally be used as reference for features common to SPR sensors 21 and 22) has only five strip electrodes 33, the number is by way of example and a number of strip electrodes other than five may be used in the practice of the present invention. For example, in some embodiments of the present invention strip electrodes 33 cover a region of sensor surface 32 having an extent in the x and the y directions equal to about 20 mm. Each strip electrode 33 has a width of, optionally, about 100 micrometers and the electrodes are optionally formed on sensor surface 32 at a pitch of about 200 micrometers. For these dimensions the number of strip electrodes 33 on sensor surface 32 is about 100.

Microchannels 36 in flow cell 34 are optionally parallel and flow cell 34 is mounted to prism 30 so that the microchannels are optionally perpendicular to strip-electrodes 33. Each microchannel 36 optionally has an inlet segment 55 and a segment 56 that is open on a side of the microchannel facing sensor surface 32 so that fluid flowing in the microchannel contacts each strip electrode 33 that the microchannel crosses at a crossover region 58. Regions of some microchannels 36 in SPR sensor 20 in FIG. 1A are cut away to show crossover regions 58. Each microchannel 36 optionally has an open ended outlet segment 61 through which fluid flowing in the microchannel may exit the microchannel.

In accordance with an embodiment of the present invention, each strip electrode 33 is connected to a power supply 60. Power supply 60 is controllable to electrify each strip electrode 33 relative to a suitable reference electrode connected to the power supply so as to generate an electric field having a component perpendicular to sensor surface 32 at each of the electrode's cross over regions 58. The electric field at each cross over region passes through the lumen of the microchannel 36 that crosses over the electrode at the crossover region. To appropriately electrically isolate each strip electrode 33, flow cell 34 is formed from an insulating material or is appropriately covered with an insulating material. For convenience of presentation it is assumed hereinafter that flow cell 34 and other flow cells, in accordance with an embodiment of the present invention, are formed from a suitable insulating material although parts of the flow cell may be formed from a conducting material.

In some embodiments of the present invention, as shown for SPR sensor 20 in FIG. 1A, each strip electrode 33 is electrified relative to a same relatively large reference electrode 62 located on a top surface 64 of flow cell 34. In some embodiments of the present invention, reference electrode 62 is "buried" in flow cell 34 so as to bring each strip electrode closer to the large electrode. Bringing reference electrode 62 closer to strip electrodes 33 tends to concentrate the electric field between an electrified strip electrode 33 and the reference electrode within a volume of space sandwiched between the strip electrode and the reference electrode and thereby reduce "cross-talk" between strip electrodes.

In some embodiments of the present invention top surface 64 has a recessed portion relatively closer to strip electrodes 33 than other regions of the top surface. Reference electrode 62 is mounted to the recessed portion so as to reduce distance between the reference electrode and strip-electrodes 33. FIG. 1C schematically shows an SPR sensor 70, in accordance with an embodiment of the present invention similar to SPR sensor in which a top surface 72 of a flow cell 74 has a recessed portion 75 on which a reference electrode 62 is mounted. For clarity of presentation in FIG. 1C internal microchannels, other internal features of flow cell 74 and strip electrodes 33 are not shown.

In some embodiments of the present invention each strip electrode 33 has its own exclusive "partner" reference electrode relative to which the strip electrode is electrified by power supply 60. Such a partner electrode is optionally a mirror image of the strip electrode to which it is a partner. Optionally, each strip electrode's partner electrode is buried inside flow cell 34. FIG. 1D schematically shows an SPR sensor 80 having a flow cell 82, in accordance with an embodiment of the present invention, in which each strip electrode 33 has its own mirror image partner electrode 83 buried in the flow cell.

In some embodiments of the present invention an SPR conductor on sensor surface 32 comprises a plurality of pixel electrodes instead of strip-electrodes 33. FIG. 1E schematically shows an SPR sensor 140 comprising an SPR conductor having pixels electrodes 142. For clarity of presentation internal features of flow cell 34 are not shown in FIG. 1E and the flow cell and reference electrode 62 are shown in ghost lines. Pixel electrodes 142 are arrayed in optionally parallel rows 144, each of which is optionally perpendicular to microchannels 36 (FIG. 1A) in flow cell 34 and each flow cell in a row 144 is located under a different microchannel. Each pixel electrode 142 is connected to power supply 60 and may be electrified relative to reference electrode 62 independent of electrification of the other pixel electrodes.

In some embodiments of the present invention both an SPR conductor and a reference conductor or conductors are located on an SPR sensor surface. By way of example, FIG. 1F schematically shows an SPR sensor 150, in accordance with an embodiment of the present invention having an SPR conductor comprising a plurality of strip electrodes 152 and a reference electrode 154 both of which are located on the SPR sensor's sensor surface 32. Reference electrode 154 is in the form of a comb having teeth 156 that interleave with strip electrodes 152 and is a reference electrode common to all the strip electrodes. Optionally reference electrode 152 is grounded. Each strip electrode 152 is electrified by power supply 60 relative to reference electrode 154 independent of the electrification of other of the strip electrodes.

In accordance with an embodiment of the present invention, a flow cell is formed from an elastic material and liquids are introduced into a microchannel formed in the flow cell by puncturing the elastic material with a flow needle until an outlet orifice of the flow needle is substantially aligned with the microchannel. Liquid is pumped into the microchannel from the flow needle's lumen to the microchannel via the orifice. Any of various methods and "positioning" apparatus known in the art may be used to control movement and positioning of the flow needles and controlling liquid flow into and out of the flow needles. A method of controlling fluid flow in microchannels of a flow cell using flow needles, in accordance with an embodiment of the present invention is discussed with reference to FIG. 1A.

Liquids are introduced into microchannels 36 of flow cell 34 shown in FIG. 1A either through their respective inlet segments 55 or by injection through flow needles 42. Each microchannel 36 is associated with its own flow needle 42 and position of the flow needle determines whether liquid from inlet segment 55 or from flow needle 42 flows in the microchannel. Each microchannel 36 is also associated with its own drain microchannel 59. A microchannel 36 and its drain microchannel 59 are not connected by a flow channel formed in the flow cell 34.

Each flow needle 42 has an outlet orifice 43 optionally located along the length of the flow needle that communicates with the flow needle's lumen and an optionally closed, relatively sharp tip 45. Optionally, a depression 47, i.e. a "shunt depression 47" is formed on a "back-side" wall 49 of flow needle 42 opposite its outlet orifice 43. Inset 90 in FIG. 1 shows a schematic enlarged view of a flow needle 42 that shows back-side wall 49 of the flow needle and its shunt depression 47.

Whereas in FIG. 1A shunt depression 47 has a width less than a width of backside wall 49 in some embodiments of the present invention, shunt depression 47 has a width substantially equal to that of backside wall 49 and such a width can be advantageous. It is noted that whereas flow needles 42 have their respective orifices 43 located along their lengths and are shown with closed ends, flow needles suitable for the practice of the present invention may have open ends and these open ends may function also as exit orifices.

In accordance with an embodiment of the present invention, a flow needle 42 has an extracted position and an inserted position. In FIG. 1A all flow needles 42 are shown in the extracted position. In the extracted position a flow needle 42 does not affect fluid flow in its associated microchannel 36 and liquid pumped into inlet segment 55 of the associated microchannel will flow in the microchannel.

To move flow needle 42 from its extracted position to its inserted position, in accordance with an embodiment of the present invention, the flow needle is forced into flow cell 34 so that it cuts through and penetrates the elastic flow cell material. The flow needle is inserted until the flow needle's orifice 43 is substantially aligned with the lumen of its associated microchannel 36. In the inserted position flow needle 42 blocks liquid flow from inlet segment 55 of microchannel 36 into the microchannel's lumen downstream of the inlet segment and enables flow of liquid from the flow needle's lumen into the microchannel. For those flow needles 42, which in accordance with an embodiment of the present invention have a shunt depression, in the inserted position the flow needle shunts liquid pumped into inlet segment 55 of microchannel 36 to the microchannel's drain microchannel 59.

Figure 2:
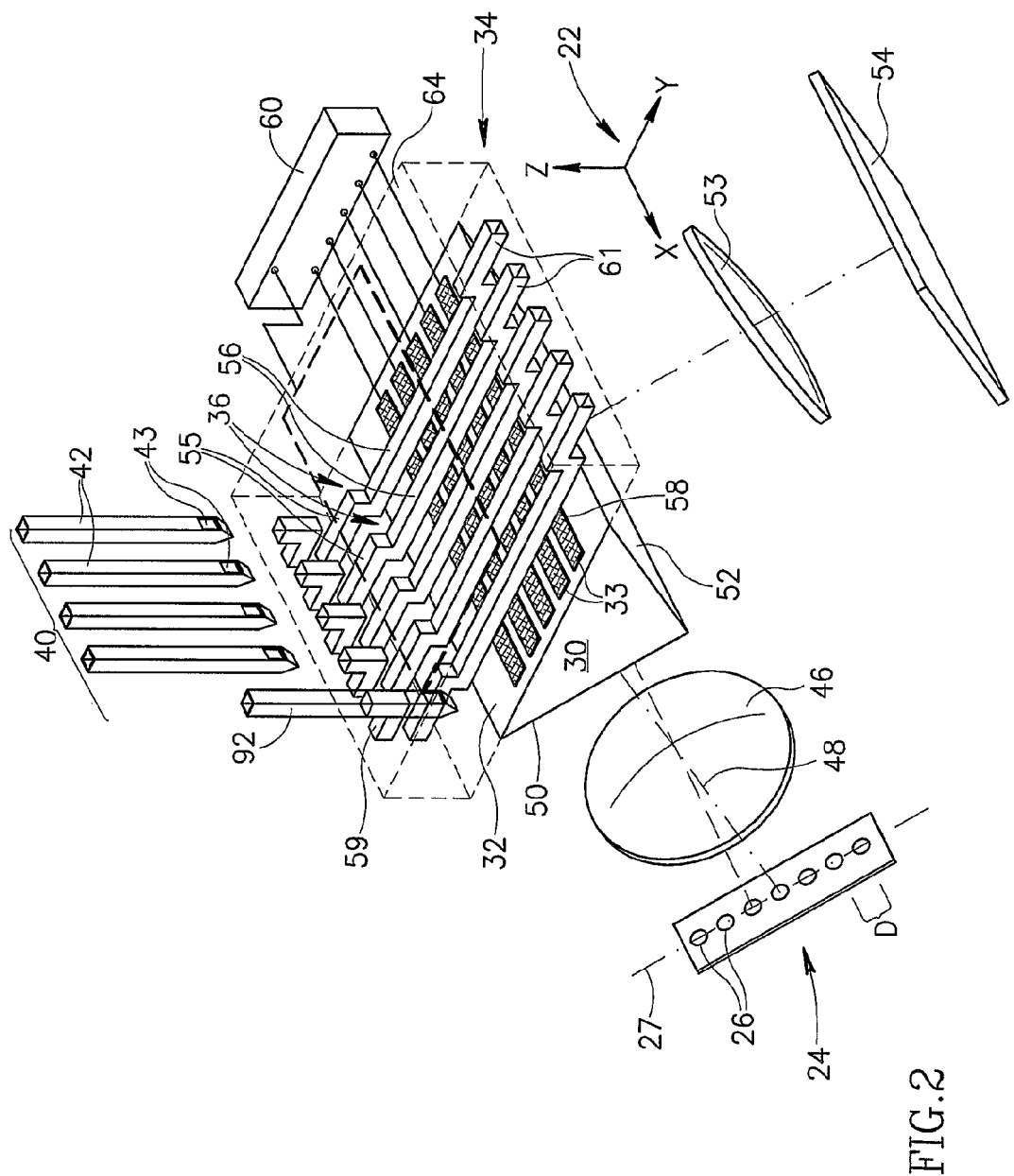
FIG. 2 schematically shows an SPR sensor with a flow needle inserting fluid into a microchannel, in accordance with an embodiment of the present invention.

FIG. 2 schematically shows SPR sensor 20 with a left-most flow needle 42, which is individualized by the numeral 92, in an inserted position. FIGS. 3A-3D schematically illustrate cross sectional views of flow needle 92 being moved from its extracted position to its inserted position in flow cell 34. In the cross-sectional views, orifice 43 of flow needle 92 is indicated by a gap in the wall of the flow needle and shunt depression 47 as a recess in the wall.

Figure 3A:
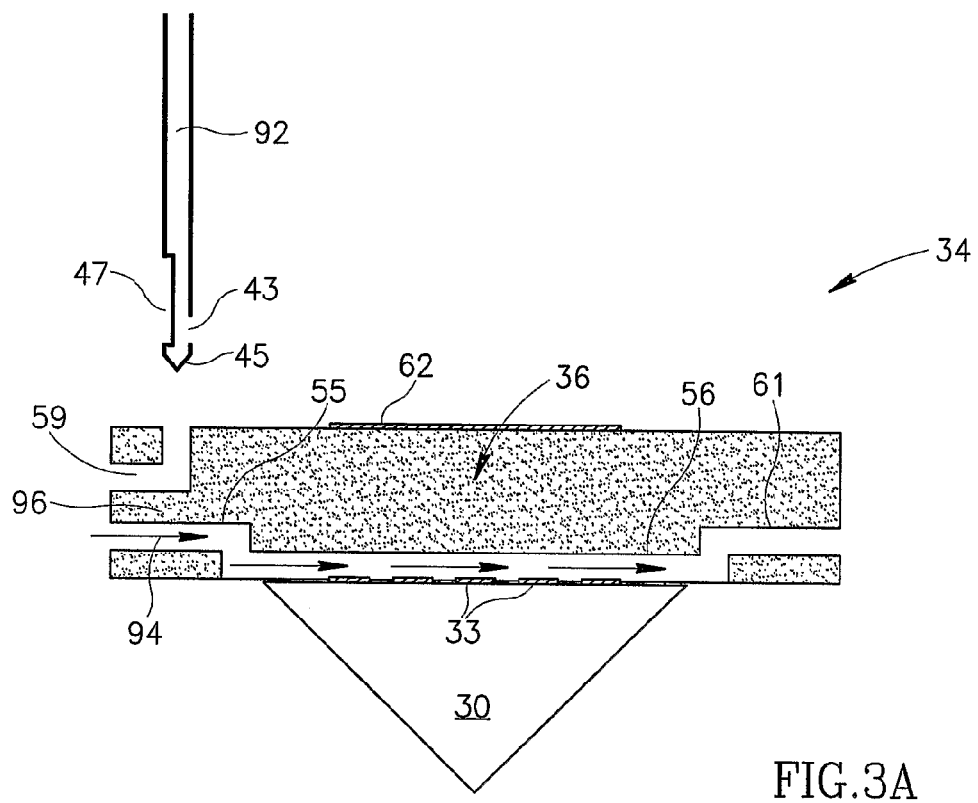
FIGS. 3A-3D show schematic cross section views illustrating a process by which a flow needle punctures a flow cell in order to insert fluid into a microchannel in the flow cell and shunt fluid flowing into the microchannel to a drain microchannel, in accordance with an embodiment of the present invention.
Figure 3B:
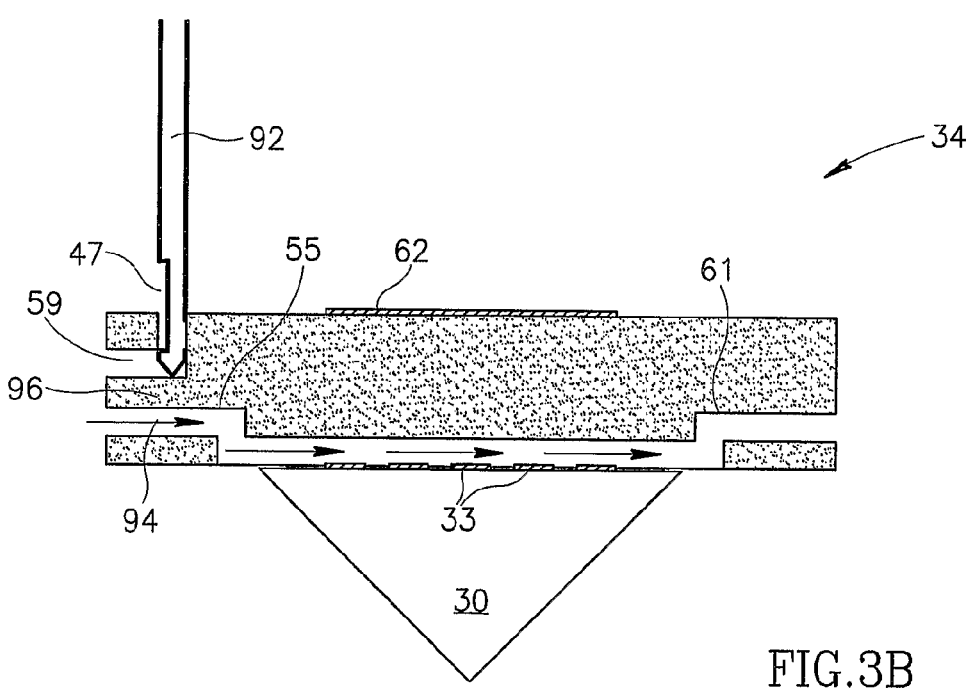
Figure 3C:
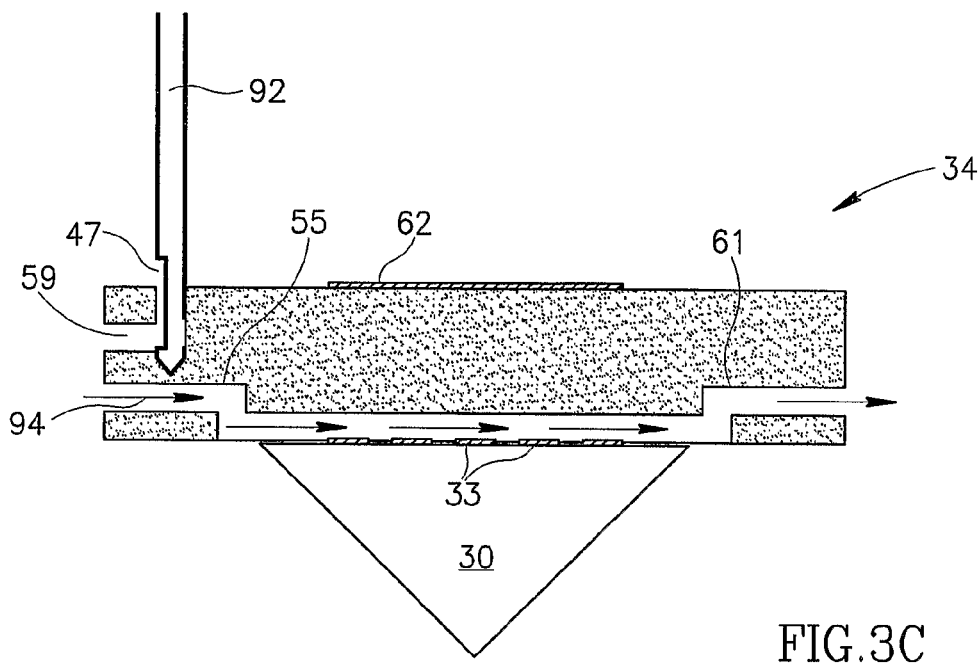

In FIG. 3A flow needle 92 is in the extracted position and liquid, indicated by arrowhead lines 94 is being pumped into inlet segment 55 of its associated microchannel 36 from a suitable source. Liquid 94 flows freely from inlet segment 55 into and through microchannel 36. In FIG. 3B flow needle 92 is lowered into drain microchannel 59 until its tip 45 is touching a region 96, hereinafter referred to as a "septum 96", of flow cell 34 that separates drain microchannel 59 from microchannel 36. In FIG. 3C flow needle 92 is schematically being forced through septum 96.

Figure 3D:
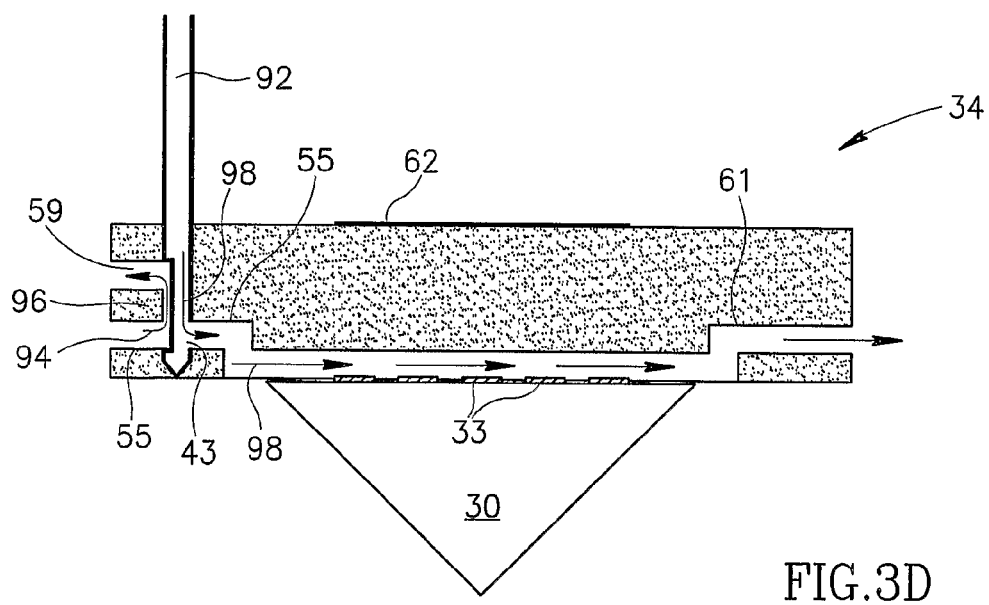

In FIG. 3D, flow needle 92 has penetrated flow cell 34 sufficiently so that its outlet orifice 43 is substantially aligned with microchannel 36 and the flow needle is in its inserted position. In addition, in the inserted position, shunt depression 47 is substantially aligned to form a shunt flow channel between inlet segment 55 and drain microchannel 59. Shunt depression 47 is sufficiently deep and narrow so that the elastic material of flow cell 34 does not squeeze into the shunt depression and seal it. Liquid represented by arrowhead lines 98 flows from flow needle 92 through the flow needle's exit orifice 43 into microchannel 36. Flow of liquid 94 from inlet segment 55 into a portion of microchannel 36 downstream of the flow needle is substantially blocked by the flow needle and is shunted via shunt depression 47 to drain microchannel 59, from which drain microchannel the liquid exits flow cell 34.

In some embodiments of the present invention to provide for a degree of play in alignment of exit orifice 43 with microchannel 36 when flow needle 92 is in the inserted position, microchannel 36 has a relatively enlarged cross section in a region of the microchannel in which the flow needle is introduced. Alternatively or additionally exit orifice 43 may be smaller than the microchannel cross section in the region of the microchannel in which flow needle 92 is introduced.

Whereas in the above example flow cell 34 is assumed to be formed from an elastic material, in some embodiments of the present invention, a flow cell is formed from a relatively inelastic material. To provide regions of a microchannel for which a flow needle can be introduced into the microchannel, in accordance with an embodiment of the present invention, the flow cell comprises elastic inserts, which form regions of the microchannel. A flow needle may positioned in the flow channel, in accordance with an embodiment of the present invention by suitable puncturing the elastic inserts.

FIG. 3E schematically shows a cross sectional view of a flow cell 160 having a microchannel 162 formed therein, in accordance with an embodiment of the present invention. Flow cell 160 is produced from a relatively inelastic material and to provide a suitable region through which to introduce a flow needle into microchannel 162, in accordance with an embodiment of the resent invention, the flow cell is fitted with elastic inserts 164 and 166. A channel 59 has a portion thereof formed in the relatively inelastic material of flow cell 160 and a portion thereof formed in elastic insert 164.

It is noted that in FIGS. 3A-3E it is assumed that fluid introduced into a microchannel 36 by flow needle 92 exits the flow channel through open ended exit segment 61. In some embodiments of the present invention fluid introduced into a microchannel via a first flow needle may exit the flow channel via a second flow needle rather than through an exit segment. Both the first and second flow needles puncture regions of the wall of the microchannel formed form an elastic material and are introduced into the lumen of the microchannel so that their respective orifices communicate with the lumen. The orifice of the first flow needle faces downstream and the orifice of the second flow needle faces upstream. Fluid is introduced into the microchannel via the first needle, for example by pumping the fluid into the microchannel via the first needle's lumen.

The fluid exits the microchannel via the second flow needle, for example by aspirating the fluid from the microchannel via the second needle's lumen.

It is further noted that in the discussion of FIGS. 1A-3E when a flow needle 42 (FIGS. 1A-2) or individualized flow needle 92 (FIGS. 3A-3D) is introduced into microchannel 36 it completely blocks fluid flow into the microchannel from upstream of the needle. In some embodiments of the present invention a flow needle may only partially block fluid flow from upstream of the needle. For example, the orifice of the flow needle may be positioned so that the needle may the orifice communicates with the microchannel lumen when the flow needle is only partially introduced into the microchannel lumen so that it only partially blocks fluid flow from upstream. Alternatively the flow needle may be narrower than a width of the cross section of the microchannel in a region of the microchannel in which the flow needle is introduced into the microchannel. As a result, even when fully introduced into the microchannel a fluid from upstream may stream downstream around the needle. A flow needle and microchannel configuration that enables the flow needle to only partially block fluid flow in the microchannel can be advantageous when it is desired to mix a fluid introduced into the microchannel via the flow needle with fluid flowing downstream from upstream of the needle. Variations of the methods described for using flow needles, in accordance with an embodiment of the present invention to introduce and remove fluid from a microchannel will occur to a person of the art.

To illustrate operation of SPR sensor 20, in accordance with an embodiment of the present invention, assume that it is required to determine the kinetics of interaction between a plurality of different "probe" proteins with a particular "target" proteins. By way of example, assume that the number of the plurality of probe proteins is equal to the number (twenty five) of crossover regions 58 between microchannels 36 and strip electrodes 33 in SPR sensor 20 and that a different probe protein is to be immobilized at each crossover region. Immobilization at cross over region, in accordance with an embodiment of the present invention, may be made directly to the conductor from which strip electrodes 33 are formed or to a suitable molecular layer formed on the conductor using any of various methods known in the art.

To prepare an appropriate microarray of the probe proteins on strip electrodes 36, initially, buffer or water is pumped through microchannels 36 via inlet segments 55 to clean and prepare the strip electrodes for immobilization of the probe proteins at crossover regions 58. Each flow needle 42 is aspirated, using any of various different methods and apparatus known in the art, with an appropriate solution comprising a different one of the plurality of probe proteins. Assume that the different probe proteins are to be immobilized on a first one of strip electrodes 33. The first strip electrode is electrified positive or negative with respect to reference electrode 62 depending upon whether the probe proteins are negatively or positively charged respectively. The remaining strip electrodes are all electrified with respect to electrode 62 to voltage or voltages having polarity opposite to polarity of a voltage to which the first electrode is electrified. Flow needles 42 with their respective nucleotide solutions are controlled to puncture flow cell 34 so that they are positioned in their inserted positions.

Upon insertion of flow needles 42 to their inserted positions, flow of buffer or water through the microchannels via their respective input segments 55 is halted and buffer or water pumped the input segments is shunted to corresponding drain microchannel 59 via the flow needle's shunt depressions 47. The probe protein solution in each flow needle 42 is pumped out of the flow needle and into its associated microchannel 36. As a result of the electrification pattern of strip electrodes 33 and the charge on the probe protein in the solution, the probe protein is attracted to the first strip electrode 33 and repelled by the other strip electrodes 33. The probe protein is thereby immobilized at the at the crossover region 58 of the associated microchannel 33 and the first strip electrode 33 and is substantially prevented from immobilizing at crossover regions 58 of the other strip electrodes 33.

During immobilization of the probe proteins, the process of immobilization and quantities of probe proteins immobilized at crossover regions 58 is monitored by performing an SPR angular scan of sensor surface 64. Light sources 26 in array 24 are sequentially turned on and turned off to perform the angular SPR scan of sensor surface 64 and illuminate substantially a same region of sensor surface 64, which includes at least all of crossover regions 58, at a plurality of different incident angles.

Signals generated by CCD 54 responsive to light from each light source 26 reflected at each crossover region 58 (i.e. from a region of sensor surface 64 on which the crossover region is located) of the first strip electrode 33 are used to determine an SPR parameter for the crossover region. The SPR parameter is used to monitor accretion of immobilized probe protein at the crossover region. Signals from crossover regions 58 of other strip electrodes 33 and from regions of strip electrodes 33 that are not crossover regions are used to correct and normalize signals from crossover regions 58 of the first strip electrode 33.

Flow needles 42 are then extracted from flow cell 34. Upon extraction blockage of inlet segments 55 of microchannels 36 by flow needles 42 is removed and "insertion holes" formed in the elastic material from which flow cell 34 is formed due to insertion of flow needles 42 seal. Flow of buffer or water through microchannels 36 via inlet segments 55 resumes and purges probe proteins at crossover regions of the first strip electrode 33 and other strip electrodes 33 and in microchannels 33 that were not immobilized.

The above-described process is repeated for each of the other strip electrode 33 with solutions containing different probe proteins from the plurality of probe proteins until a different desired one of the probe proteins is immobilized at each of crossover regions 58 and the desired microarray of twenty-five probe proteins is prepared.

Following preparation of the microarray, each of flow needles 42 is aspirated with a solution of the particular target protein whose interaction kinetics with the probe proteins is to be tested. The flow needles are inserted into flow cell 34 to their respective inserted positions to block flow of water or buffer from inlet segments 55 and flush each microchannel 36 with the target protein solutions. An angular SPR scan of sensor surface 62 is performed by appropriately turning on and off light sources 26. Signals provided by CCD 54 responsive to light from the light sources reflected from each crossover region 58 are processed to monitor the interaction kinetics between the target protein and the probe protein immobilized at the crossover region.

In the above example, interaction kinetics of a single target protein with each of twenty five probe proteins is monitored by SPR sensor 20. It is of course possible, in accordance with an embodiment of the present invention, to flow a different target protein through each microchannel after preparation of the microarray. In that case interaction kinetics of each of five target proteins is monitored for each of five different probe proteins. Interaction kinetics of a given target protein is monitored for probe proteins that are immobilized at crossover regions between each of strip electrodes 33 and a particular microchannel through which the given target protein flows.

It is further noted that in describing preparation of the above noted microarray of twenty five probe proteins, it was tacitly assumed that in order to configure electrification of strip electrodes 33 when immobilizing the proteins, all proteins pumped through microchannels 36 at a same time carry a same polarity charge. Therefore, for the resulting microarray probe proteins immobilized on crossover regions 58 of a same given strip electrode 33 carry a same polarity charge. However, in some embodiments of the present invention biomolecules having different polarity charges are immobilized on a same given strip electrode 33.

In general, biomolecules bound to a strip electrode 33, for example by covalent bonds, are bound by electrical fields that are substantially stronger than electric fields used to attract or repel biomolecules that are generated by electrifying the strip electrode. As a result, it is possible to bind biomolecules having opposite polarity charge to a same electrode strip 33.

For example, assume a first fluid comprising first biomolecules having a first polarity charge are pumped through a flow channel 36 so as to contact a given strip electrode 33 at a first cross over region 58. To attract and immobilize the first biomolecules on the first crossover region 58, the given strip electrode is appropriately electrified to attract the first biomolecules. Subsequently a second fluid comprising second biomolecules having a second polarity charge is pumped through a different flow channel 36 so as to contact the given strip electrode 33 at second crossover region 58. To attract and immobilize the second biomolecules to the second crossover region 58 of strip electrode 33 polarity of electrification of the strip electrode is reversed. The electric field generated by the reversed polarity electrification of the given strip electrode 33, while sufficient to attract the second biomolecules to the strip electrode, is not strong enough to sunder bonds between the first biomolecules, which are already bound to the strip electrode, and the strip electrode.

It is noted that an SPR electrode comprising a plurality of pixel electrodes, in accordance with an embodiment of the present invention, such as the SPR electrode comprising pixel electrodes 142 shown in FIG. 1E, may be advantageous in preparing a microarray of biomolecules having different polarity charge configurations. A "pixelated" SPR electrode, in accordance with an embodiment of the present invention, provides increased flexibility for generating different polarity electric fields at different regions of the SPR electrode.

In the above description of exemplary SPR sensors, in accordance with embodiments of the present invention, only angular SPR scans are used to monitor processes occurring at a microarray prepared on an SPR electrode formed on sensor surface 32. Some SPR sensors, in accordance with embodiments of the present invention, are configured to provide wavelength scans of a sensor surface and comprise a light source array that provides light at a same incident angle and different wavelengths.

Figure 4:
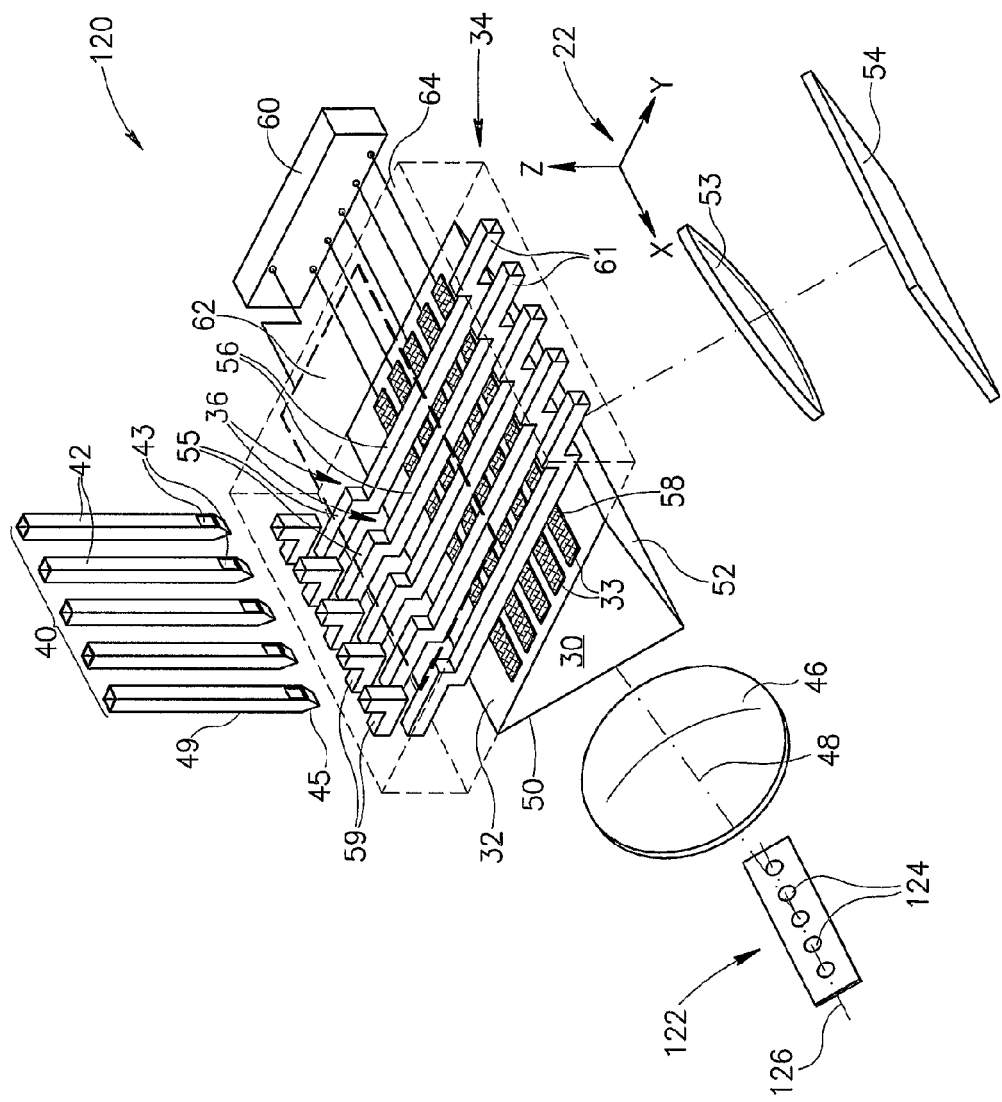
FIG. 4 schematically shows an SPR sensor, for performing an SPR wavelength scan of a sensor surface, in accordance with an embodiment of the present invention.

FIG. 4 schematically shows an SPR sensor 120, in accordance with an embodiment of the present invention, configured to provide SPR wavelength scans of sensor surface 32 at a constant incident angle. SPR sensor 120 is similar to SPR sensor 20 shown in FIG. 1A. However, unlike SPR sensor 20, SPR sensor 120 optionally comprises a linear light array 122 of light sources 124 for which each light source provides light at a different desired wavelength and an array axis 126 of the array is parallel to the x-axis.

Incident angle of light from a light source, such as a light source 26 in array 24 of SPR sensor 20 (FIG. 1A) or a light source 124, is determined substantially only by an elevation angle of the light source position measured with respect to the z-axis. The incident angle is a second order function of an azimuth angle, as measured for example from the x-axis and in the xy-plane, of a light source 26 or a light source 124.

Whereas each light source 26 in SPR sensor 20 (FIG. 1A) is located at a same azimuth angle (all light sources 26 are located substantially in the yz-plane) but at a substantially different declination angle, light sources 124 in array 120 are located at a substantially same declination angle but substantially different azimuth angles. Different light sources 26 therefore provide, in accordance with an embodiment of the present invention, light at different incident angles and are suitable for providing angular SPR scans of SPR sensor surface 32 at constant wavelength. Light sources 124 on the other hand provide light at substantially a same incident angle but at different wavelengths and light source array 122 is therefore suitable for providing an SPR wavelength scan of sensor surface 32 at a constant incident angle.

In accordance with some embodiments of the present invention, an SPR sensor comprises a two dimensional, optionally planar, array of light sources. In some embodiments of the present invention, light sources are configured in the array so that they provide light at different wavelengths and from a range of elevation angles and a range of azimuth angles. By appropriately turning on and off light sources in the array, both SPR angular and wavelength scans of an SPR sensor surface can be provided.

Figure 5:
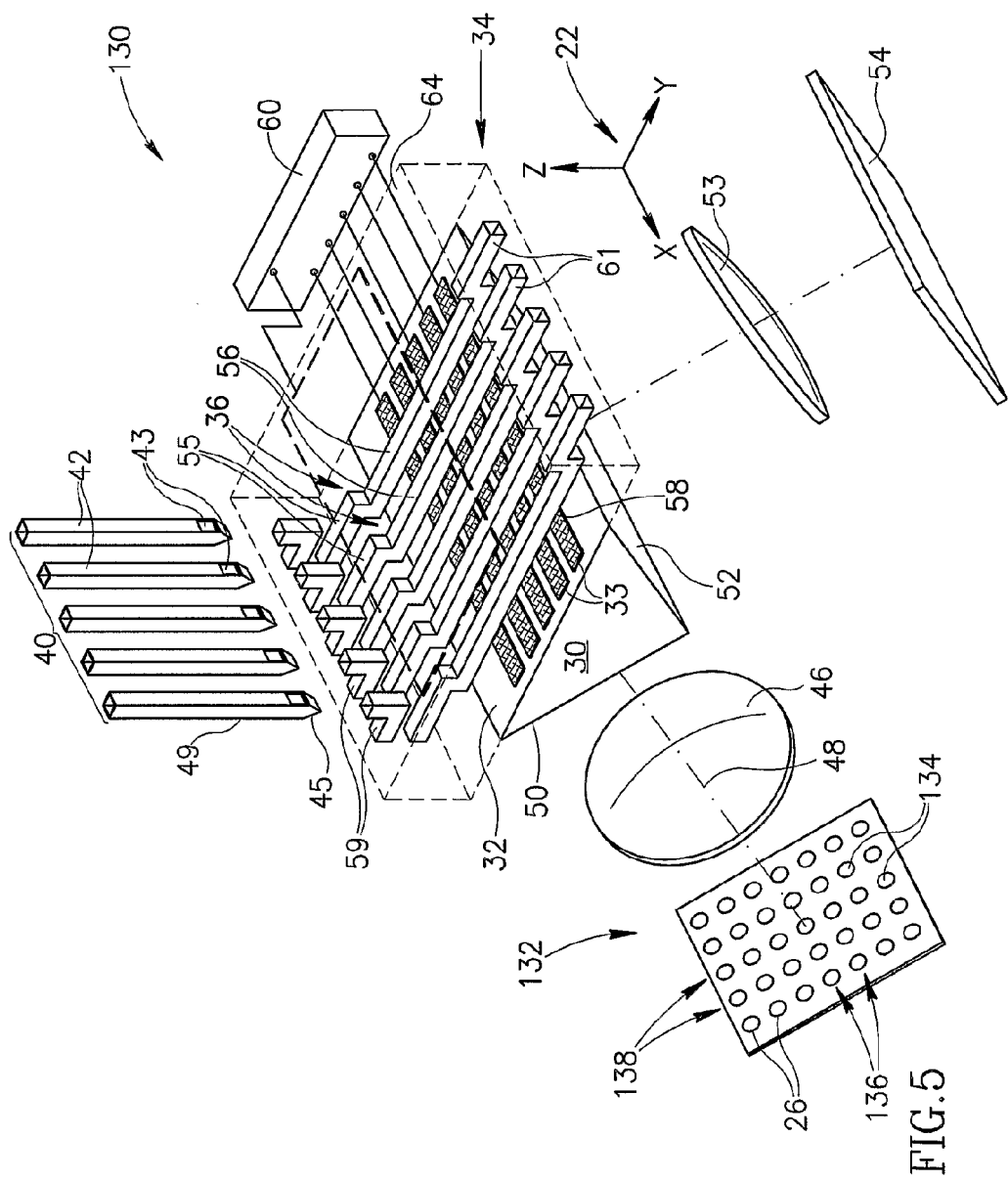
FIG. 5 schematically shows an SPR sensor, for performing an SPR wavelength scan and/or an SPR incident angle scan of a sensor surface, in accordance with an embodiment of the present invention.

FIG. 5 schematically shows an SPR sensor 130 comprising a two dimensional array 132 of light sources 134. Array 132 is optionally a rectangular array and comprises rows 136 and columns 138 of light sources 134. Rows 136 are parallel to the x-axis and each light source 134 in a row 136 optionally provides light at a different wavelength suitable for desired SPR wavelength scans of sensor surface 32. Optionally, all light sources in a same given column 138 provide light at a same wavelength. Light sources 134 in the column 138 are suitable for providing an SPR angular scan of sensor surface 32 at the wavelength of light provided by the light sources in the column.

It is noted that for performing an angular SPR scan it can be difficult to provide a light source that provides strong intensity light for illuminating an SPR sensor surface at each of a plurality of different desired incident angles. In some embodiments of the present invention all light sources 134 in array 132 provide light at a same wavelength. For a configuration in which all light sources 134 provide light at a same wavelength light source array 132 may be used to perform an angular SPR scan with relatively intense light at each incident angle used in the scan.

For example, as noted above, each light source 134 in a row 136 of array 132 provides light at a same incident angle, which is defined substantially by the row's elevation angle. Light sources 134 in different rows 136 provide light at different incident angles. Assume that the different desired scan angles for an SPR angular scan are the different incident angles provided by light sources 134 in the different rows 136. Relatively intense light may be provided at a given desired scan incident angle by simultaneously turning on all light sources 134 in the row 136 for which the light sources provide light at the given incident angle.

Figure 1B:
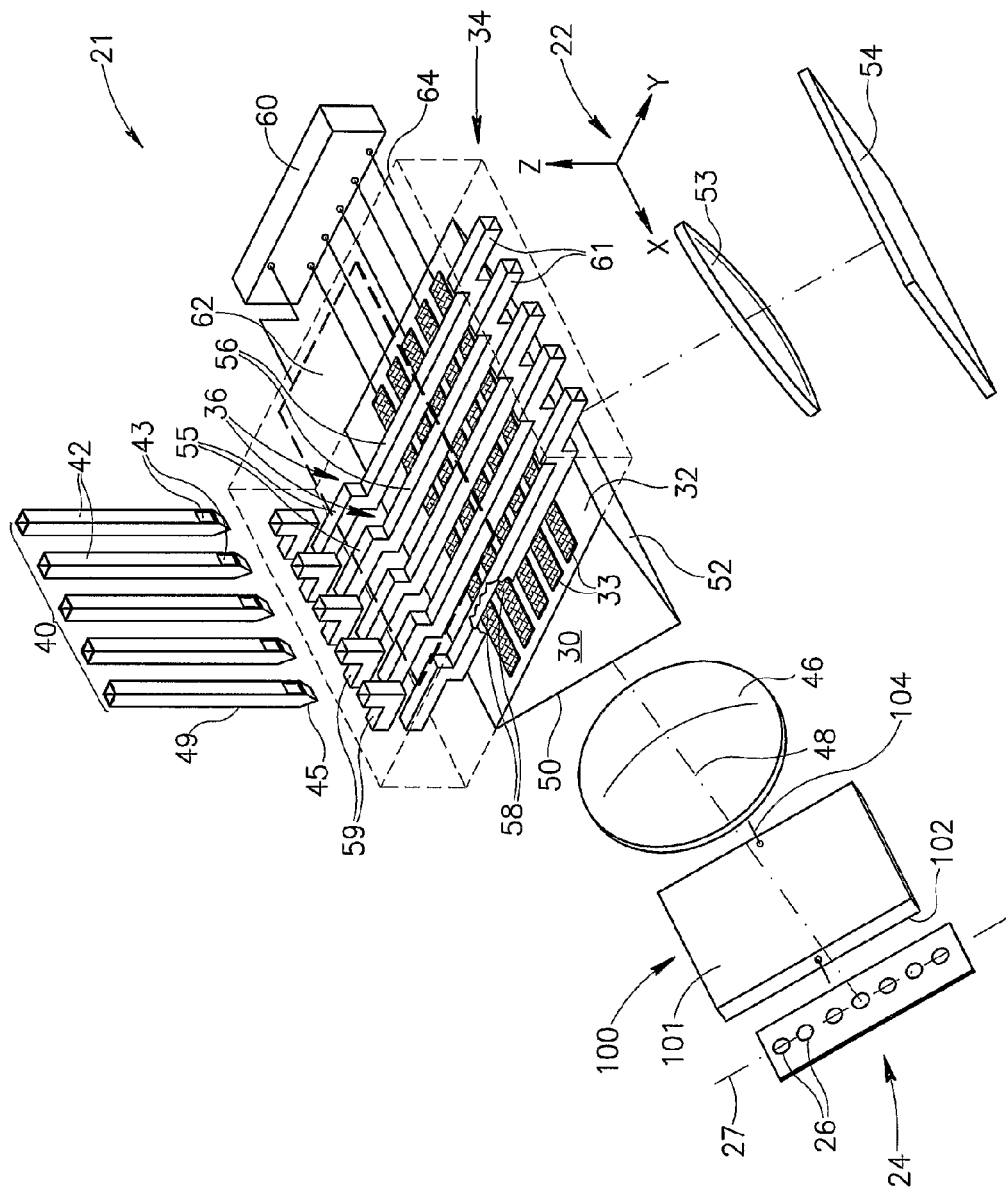
Figure 1C:
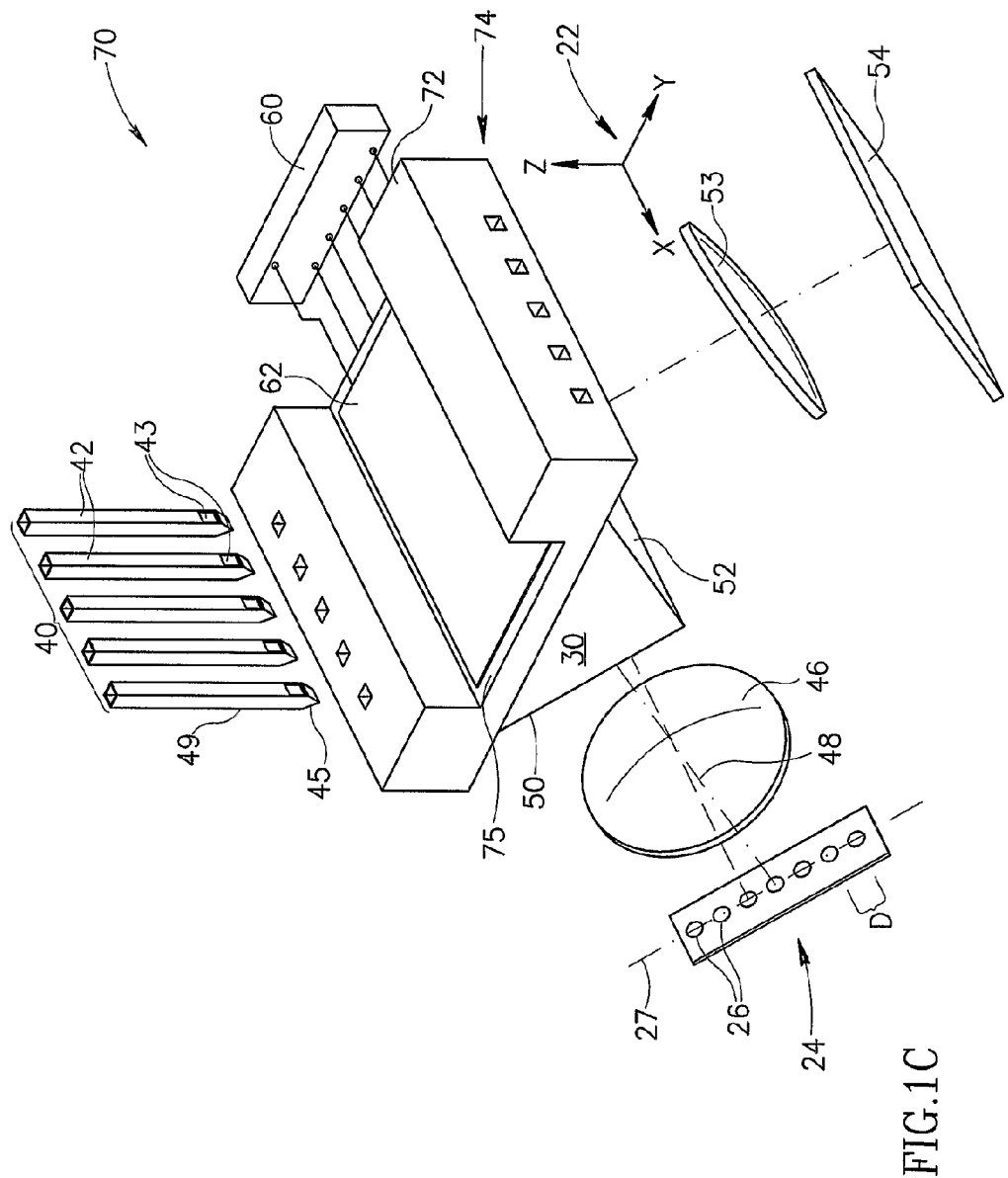
Figure 1D:
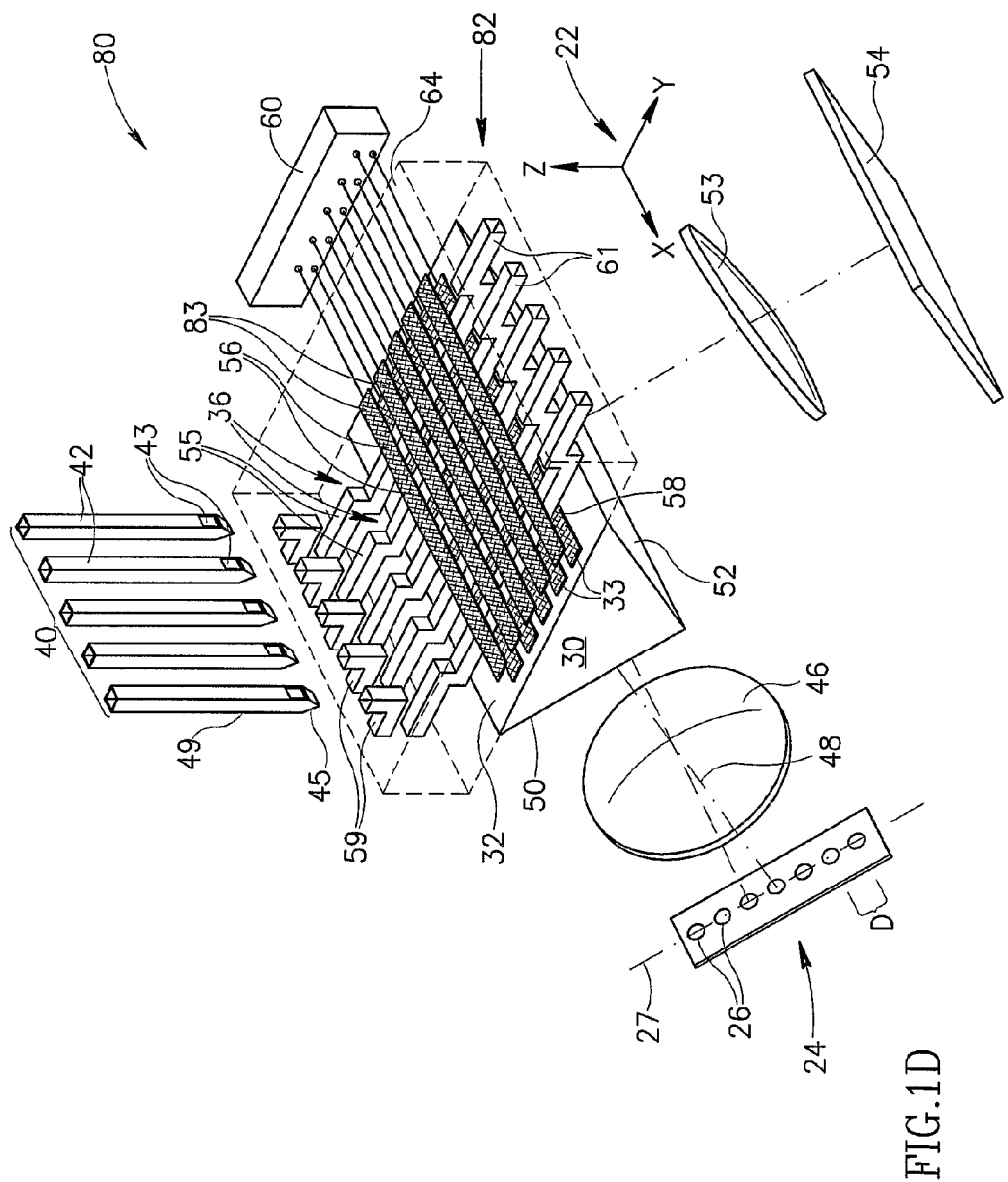
Figure 1E:
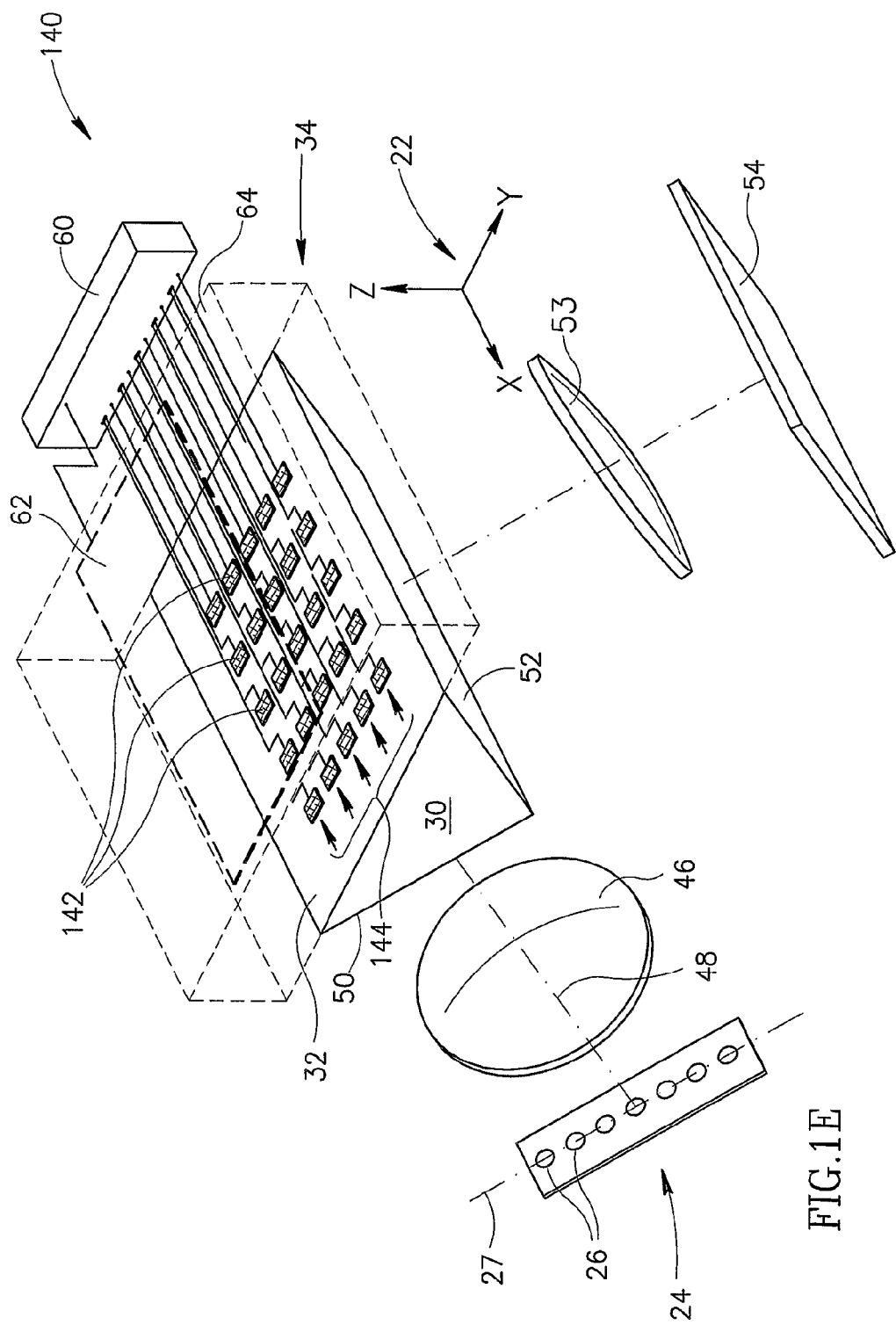
Figure 1F:
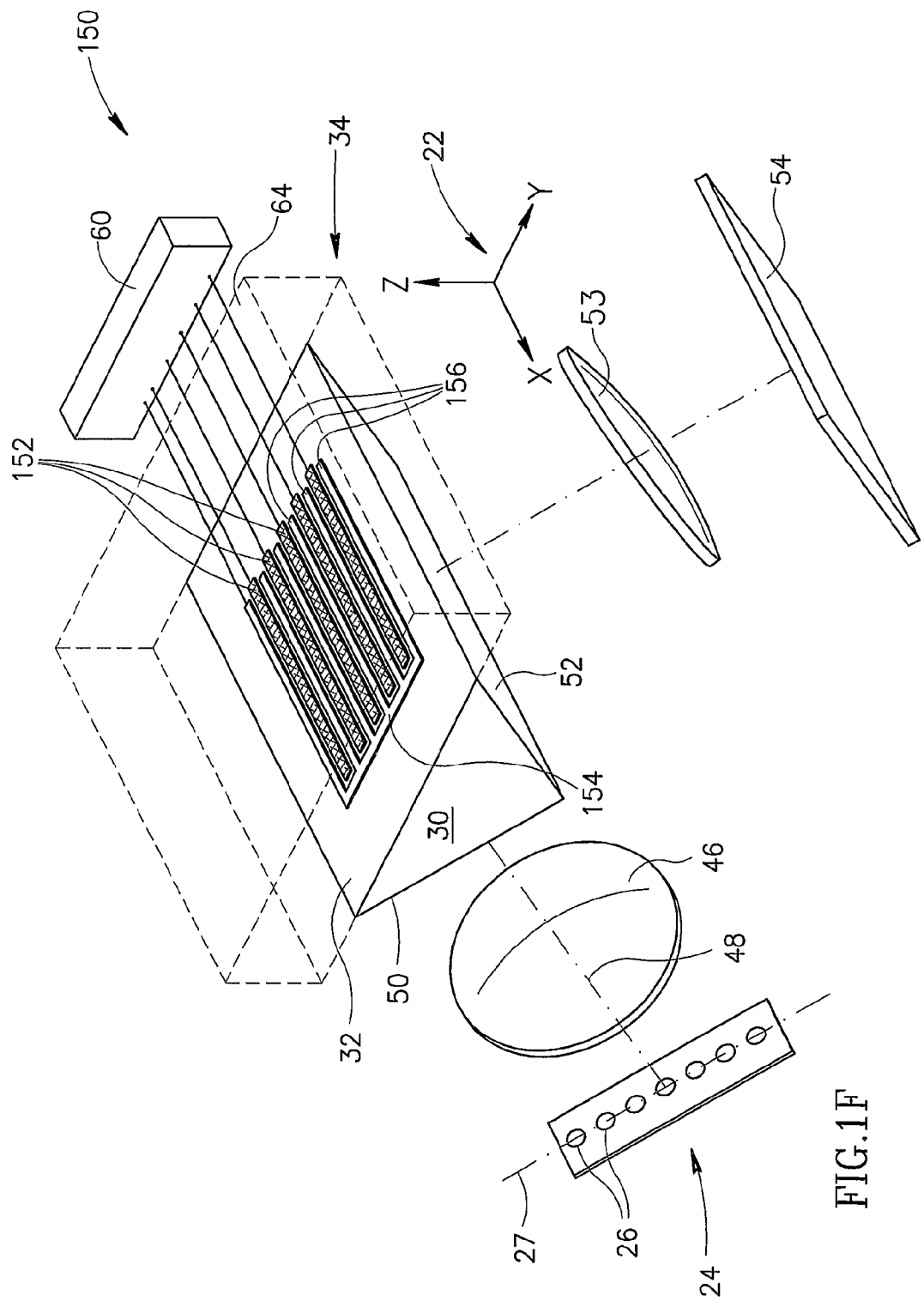

As in the case of light source array 24 (as shown in FIG. 1B), light source array 122 and a two dimensional light source array, such as array 132 shown in FIG. 5, may be combined with a displacement plate (FIG. 1B) that functions to adjust angles at which light from light sources in the array are incident on sensor surface 32.

Whereas, aspects and features of the present invention have been described as comprised in SPR sensors, the aspects and features are not limited to use in SPR sensors. For example, illumination systems, flow apparatus and electrode configurations in accordance with embodiments of the present invention may be used in critical angle refractometry systems and total internal reflection fluorescence or phosphorescence systems.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

What is claimed is:

1. A surface plasmon resonance (SPR) system using a ligand, the system comprising:
    a) a thin conducting layer suitable for SPR formed on a transparent substrate, the conducting layer comprising a plurality of electrodes;
    b) at least one flow channel crossing the electrodes at crossover regions;
    c) a power supply connected to the electrodes, and differently electrifying the electrodes at two different crossover regions, such that the ligand flowing through the flow channel is attracted to and immobilized on the electrode at one of the cross-over regions, and repelled by and substantially prevented from immobilizing on the electrode at the other of the cross-over regions; and
    d) a photosensitive surface that generates SPR signals in response to light reflected from the crossover region at which the ligand is immobilized, that can be used to determine an SPR parameter, and generates reference SPR signals in response to light reflected from the crossover region at which the ligand is prevented from immobilizing, that can be used to normalize and correct the SPR signals from the crossover region at which the ligand is immobilized.

2. A system according to claim 1, wherein the at least one flow channel comprises a plurality of flow channels.

3. A system according to claim 2, wherein the electrodes comprise a strip electrode crossed by the plurality of flow channels.

4. A system according to claim 2, wherein the electrodes comprise a pixel electrode crossed by only one of the flow channels.

5. A method for characterizing an interaction of a target material with a ligand on an SPR surface, the method comprising:
    a) electrifying a first electrode comprising a conducting layer suitable for SPR formed on a transparent substrate, so that it attracts the ligand;
    b) electrifying a second electrode differently from the first electrode, so that it repels the ligand, the second electrode also comprising a conducting layer suitable for SPR formed on a transparent substrate;
    c) passing a fluid containing the ligand through a flow channel crossed by the first and second electrodes while electrifying them, immobilizing the ligand on the first electrode and substantially not on the second electrode;
    d) passing the target material through the flow channel after the ligand has been immobilized;
    e) detecting light reflected from the first and second electrodes, after passing at least some of the target material through the flow channel;
    f) generating SPR signals from the detected light reflected from the first electrode, and SPR reference signals from the detected light reflected from the second electrode; and
    g) determining an SPR parameter that characterizes the interaction from the SPR signals, normalized and corrected by the SPR reference signals.

6. A method according to claim 5, also comprising:
    a) electrifying a third electrode, comprising a conducting layer suitable for SPR formed on a transparent substrate, that also crosses the fluid channel, after the ligand is immobilized on the first electrode, while passing fluid containing a second ligand through the flow channel, so that the second ligand is attracted to and immobilized on the third electrode, and electrifying the first and second electrodes differently so that the second ligand is repelled by and substantially not immobilized on the first and second electrodes;
    b) detecting light reflected from the third electrode, after passing at least some of the target material through the flow channel;
    c) generating additional SPR signals from the detected light reflected from the third electrode; and
    d) determining an SPR parameter characterizing an interaction of the target material with the second ligand from the additional SPR signals.

7. A system according to claim 3, wherein the strip electrode is about 100 μm in width.

8. A system according to claim 3, wherein the electrodes comprise a plurality of substantially parallel strip electrodes repeating at a pitch of about 200 μm.

9. A system according to claim 3, wherein the electrodes comprise about 100 substantially parallel strip electrodes.

10. A method according to claim 5, wherein the first electrode is a strip electrode crossed also by a second flow channel, the method also comprising:
    a) passing a fluid containing a second ligand, which has a polarity charge of a same sign as the first ligand, through the second flow channel while the first electrode is electrified so that it attracts the first and second ligands, immobilizing the second ligand on the first electrode where it is crossed by the second flow channel;
    b) passing a second target material, the same as or different from the first target material, through the second flow channel after the second ligand has been immobilized;
    c) detecting light reflected from the first electrode where it is crossed by the second flow channel, after passing at least some of the second target material through the second flow channel;
    d) generating second SPR signals from the detected light reflected from the first electrode where it is crossed by the second flow channel; and
    e) determining a second SPR parameter that characterizes an interaction of the second target material with the second ligand, from the SPR signals.

11. A method according to claim 10, wherein the second electrode is also a strip electrode crossed also by the second flow channel, the second ligand being repelled by the second electrode and substantially not immobilized on it when it is electrified differently from the first electrode, and the method also comprises detecting light reflected from the second electrode where it is crossed by the second flow channel and generating second SPR reference signals from said detected light, and determining a second SPR parameter that characterizes the interaction of the second target material with the second ligand comprises normalizing and correcting the second SPR parameter from the second reference signals.

12. A method according to claim 5, wherein the first electrode is a strip electrode crossed also by a second flow channel, the method also comprising:
  a) electrifying the first electrode so it repels the first ligand, at a different time than when the first electrode is electrified so it attracts the first ligand;
  b) passing a fluid containing a second ligand, which has a polarity charge of an opposite sign to the first ligand, through the second flow channel while the first electrode is electrified so that it repels the first ligand and attracts the second ligand, immobilizing the second ligand on the first electrode where it is crossed by the second flow channel;
  c) passing a second target material, the same as or different from the first target material, through the second flow channel after the second ligand has been immobilized;
  d) detecting light reflected from the first electrode where it is crossed by the second flow channel, after passing at least some of the second target material through the second flow channel;
  e) generating second SPR signals from the detected light reflected from the first electrode where it is crossed by the second flow channel; and
  f) determining a second SPR parameter that characterizes an interaction of the second target material with the second ligand, from the SPR signals.

13. A method according to claim 12, wherein, after one of the two ligands is immobilized on the first electrode, and it is electrified so it repels the already immobilized ligand and attracts the other ligand, the first electrode is not electrified so strongly that the already immobilized ligand is removed from it.

14. A surface plasmon resonance (SPR) system comprising:
  a) a thin conducting layer suitable for SPR formed on a transparent substrate, the conducting layer comprising a number of conducting strips about 100 µm in width;
  b) a plurality of flow channels crossing the conducting strips at crossover regions;
  c) an illumination system configured to illuminate an interface of the conducting layer and the substrate at the crossover regions, and at other regions of the conducting strips that are not crossover regions, at a plurality of different angles of incidence or different wavelengths; and
  d) a photosensitive surface that generates SPR signals in response to light reflected from the illuminated crossover regions that can be used to determine an SPR parameter, and generates reference SPR signals in response to light reflected from the other regions, that can be used to normalize or correct the SPR signals from the crossover regions.

* * * * *